United States Patent
Nakata et al.

(10) Patent No.: US 9,107,964 B2
(45) Date of Patent: Aug. 18, 2015

(54) RADIOACTIVE FLUORINE-LABELED COMPOUND

(71) Applicants: NIHON MEDI-PHYSICS CO., LTD., Koto-ku (JP); NATIONAL UNIVERSITY CORPORATION HOKKAIDO UNIVERSITY, Sapporo-shi (JP)

(72) Inventors: Norihito Nakata, Sodegaura (JP); Yuki Okumura, Sodegaura (JP); Masato Kiriu, Sodegaura (JP); Eriko Nagata, Sodegaura (JP); Hiroki Matsumoto, Sodegaura (JP); Yuji Kuge, Sapporo (JP); Songji Zhao, Sapporo (JP); Ken-Ichi Nishijima, Sapporo (JP)

(73) Assignees: NIHON MEDI-PHYSICS CO., LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 14/345,493

(22) PCT Filed: Sep. 18, 2012

(86) PCT No.: PCT/JP2012/073858
§ 371 (c)(1),
(2) Date: Mar. 18, 2014

(87) PCT Pub. No.: WO2013/042668
PCT Pub. Date: Mar. 28, 2013

(65) Prior Publication Data
US 2014/0364620 A1    Dec. 11, 2014

(30) Foreign Application Priority Data

Sep. 22, 2011 (JP) ................................. 2011-207926

(51) Int. Cl.
| | | |
|---|---|---|
| *C07D 233/91* | (2006.01) | |
| *C07D 405/06* | (2006.01) | |
| *A61K 51/04* | (2006.01) | |
| *C07B 59/00* | (2006.01) | |

(52) U.S. Cl.
CPC ........... *A61K 51/0453* (2013.01); *C07B 59/002* (2013.01); *C07D 233/91* (2013.01); *C07D 405/06* (2013.01); *A61K 2123/00* (2013.01)

(58) Field of Classification Search
CPC ............... C07D 233/91; C07D 405/06; A61K 31/0453; C07B 59/002
See application file for complete search history.

(56) References Cited

U.S. PATENT DOCUMENTS

| | | |
|---|---|---|
| 5,086,068 A | 2/1992 | Raleigh et al. |
| 5,674,693 A | 10/1997 | Raleigh et al. |
| 5,728,843 A | 3/1998 | Wallace et al. |
| 6,252,087 B1 | 6/2001 | Koch et al. |
| 7,230,115 B1 | 6/2007 | Dolbier et al. |

FOREIGN PATENT DOCUMENTS

| | | |
|---|---|---|
| JP | 06-211805 A | 8/1994 |
| JP | 06-298739 A | 10/1994 |
| JP | 2004-075564 A | 3/2004 |
| WO | WO 95/09844 A1 | 4/1995 |
| WO | WO 01/19799 A2 | 3/2001 |

OTHER PUBLICATIONS

International Search Report (PCT/ISA/210) mailed on Nov. 6, 2012, by the Japanese Patent Office as the International Searching Authority for International Application No. PCT/JP2012/073858.
Thomlinson RH and Gray LH, "The histological structure of some human lung cancers and the possible implications for radiotherapy", Br J Cancer. Dec. 9 (4): 539-49, 1955.
Kennedy KA et al., "The hypoxic tumor cell: a target for selective cancer chemotherapy", Biochem Pharmacol. Jan. 1; 29 (1): 1-8, 1980.
Brizel DM et al., "Tumor hypoxia adversely affects the prognosis of carcinoma of the head and neck", Int J Radiat Oncol Biol Phys May 1; 38: 285-289, 1997.
Hockel M et al., "Intratumoral pO$_2$ predicts survival in advanced cancer of the uterine cervix", Radiother Oncol 26 (1): 45-50, 1993.
Nordsmark M, Overgaard M, Overgaard J "Pretreatment oxygenation predicts radiation response in advanced squamous cell carcinoma of the head and neck" Radiother Oncol 41: 31-39, 1996.
Brizel DM et al., "Tumor oxygenation predicts for the likelihood of distant metastases in human soft tissue sarcoma", Cancer Res. Mar. 1; 56 (5): 941-3, 1996.
Suzuki Y et al., "Oxygenated and reoxygenated tumors show better local control in radiation therapy for cervical cancer", Int J Gynecol Cancer, Jan.-Feb.; 16 (1): 306-11, 2006.

(Continued)

*Primary Examiner* — Rebecca Anderson
(74) *Attorney, Agent, or Firm* — Buchanan, Ingersoll & Rooney PC

(57) ABSTRACT

The present invention is a compound represented by the following formula (1) or a salt thereof. In the formula (1), $R_1$ denotes a hydrogen atom, a methyl group, or a hydroxymethyl group, and n is an integer of 1 or 2.

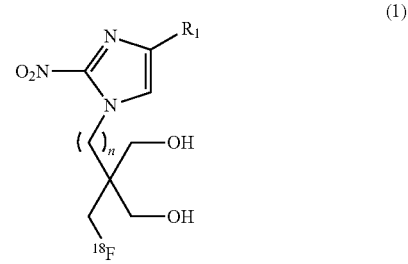

(1)

9 Claims, 8 Drawing Sheets

(56) References Cited

OTHER PUBLICATIONS

Varghese AJ et al., "Hypoxia-dependent reduction of 1-(2-nitro-1-imidazolyl)-3-methoxy-2-propanol by Chinese hamster ovary cells and KHT tumor cells in vitro and in vivo", Cancer Res. 36: 3761-3765, 1976.

Pettersen EO, "Toxic and Radiosensitizing Effect of the 2-Nitroimidazole Misonidazole (Ro-07-0582) on Murine CFU in vivo", Br. J. Cancer, 37, Suppl. III, 107-110, 1978.

Durand RE and Raleigh JA "Identification of nonproliferating but viable hypoxic tumor cells in vivo", Cancer Res 58: 3547-3550, 1998.

Nordsmark M et al., "Measurements of hypoxia using pimonidazole and polarographic oxygen-sensitive electrodes in human cervix carcinomas", Radiotherapy and Oncology; 67 (1), p. 35-44, 2003.

Hypoxyprobe™ [online], Cosmo Bio Co., Ltd., 2011 [retrieved Jun. 28, 2011], internet <URL: http://www.cosmobio.co.jp/product/signal/cat41/cat93/00220001.asp?entry_id=1465>.

Urtasun RC et al., "Measurement of hypoxia in human tumours by non-invasive spect imaging of iodoazomycin arabinoside", Br J Cancer Suppl. July; 27: S209-S212, 1996.

Iyer RV et al., "A dual hypoxic marker technique for measuring oxygenation change within individual tumors", Br J Cancer. July; 78 (2): 163-169, 1998.

Ballinger JR et al., "In Vitro and In Vivo Evaluation of a Technetium-99m-Labeled 2-Nitroimidazole (BMS181321) as a Marker of Tumor Hypoxia", J Nucl Med, 37: 1023-1031, 1996.

Strauss HW et al., "Nitroimidazoles for imaging hypoxic myocardium", J Nucl Cardiol., 2: 437-445, 1995.

Rasey JS et al., "Radiolabelled fluoromisonidazole as an imaging agent for tumor hypoxia", Int J Radiat Oncol Biol Phys, Nov.; 17 (5): 985-991, 1989.

Rasey JS et al., "Characterization of [$^{18}$F]Fluoroetanidazole, a New Radiopharmaceutical for Detecting Tumor Hypoxia" J. Nucl. Med. 40: 1072-1079, 1999.

Yang DJ et al., "Development of F-18-labeled fluoroerythronitroimidazole as a PET agent for imaging tumor hypoxia" Radiology 194: 795-800, 1995.

Evans et al., "Noninvasive Detection of Tumor Hypoxia Using the 2-Nitroimidazole [$^{18}$F]EF1", J. Nucl. Med. 41: 327-336, 2000.

Ziemer L et al., "Noninvasive imaging of tumor hypoxia in rats using the 2-nitroimidazole $^{18}$F-EF5", Eur. J. Nucl. Med. Mol. Imaging 30: 259-266, 2003.

Sorger D et al., "[18F]fluoroazomycinarabinofuranoside ($^{18}$FAZA) and [$^{18}$F]Fluoromisonidazole ($^{18}$FMISO): a comparative study of their selective uptake in hypoxic cells and PET imaging in experimental rat tumors", Nucl. Med. Biol. 30: 317-326, 2003.

Piert M, et al., "Hypoxia-specific tumor imaging with $^{18}$F-fluoroazomycin arabinoside", J Nucl Med, Jan.; 46 (1): 106-13, 2005.

Yamamoto F et al., "Synthesis and Evaluation of 4-Bromo-1-(3-[$^{18}$F]fluoropropyl)-2-nitroimidazole with a Low Energy LUMO Orbital Designed as Brain Hypoxia-Targeting Imaging Agent", Biol. Pharm. Bull. 25: 616-621, 2002.

Notification of Transmittal of Translation of the International Preliminary Report on Patentability (Forms PCT/IB/338 and PCT/IB/373) and the Written Opinion of the International Searching Authority (Form PCT/ISA/237) issued on Mar. 25, 2014, by the International Bureau of WIPO in corresponding International Application No. PCT/JP2012/073858 (6 pages).

(a) (b) (c)

(a) (b) (c)

(a)  (b)

(a)  (b)

(a)  (b)

(a)  (b)

RADIOACTIVE FLUORINE-LABELED COMPOUND

TECHNICAL FIELD

The present invention relates to a radioactive fluorine-labeled compound.

RELATED ART

A hypoxic state provides important information regarding physiology, pathology, and proliferative tissue such as a tumor. In the interior of a solid tumor, since the formation of blood vessels and capillary vessels is insufficient, the tumor is placed in a state in which nutrients and oxygen are deficient, and it survives in a hypoxic state until it dies. Due to the concentration of oxygen, which has excellent radiosensitivity, being low, tumor cells in a seriously hypoxic state acquire the property of exhibiting resistance to radiotherapy. It has been reported that in chemotherapy also it is difficult to deliver a drug due to ischemia caused by a fully-functioning blood vessel structure being incomplete, and the prognosis is poor (Non-patent Documents 1 to 5).

In order to study such refractoriness of tumors and develop and evaluate new therapeutic methods, a method of identifying in vivo a hypoxic region formed from cells in a hypoxic state and quantitatively evaluate the level of hypoxia is important. As a method of identifying a hypoxic region, for example, a method employing an oxygen electrode is known (Non-patent Documents 3, 6, and 7).

On the other hand, as a representative indicator compound for a hypoxic region that has been studied for a long time, there is misonidazole, which has a 2-nitroimidazole skeleton. This compound undergoes nitroreduction under hypoxic conditions and accumulates within a cell as an electrophilic chemical species that forms an adduct with cellular macromolecules such as DNA or protein (Non-patent Documents 8 and 9).

A large number of hypoxic region indicators have been developed so far by utilizing the properties of the 2-nitroimidazole skeleton. For example, pimonidazole (1-(2-hydroxy-3-piperidinopropyl)-2-nitroimidazole), which is a weakly basic 2-nitroimidazole derivative, is used for measurement of a hypoxic region in an immunohistochemistry test based on an antibody (Patent Documents 1, 2, Non-patent Documents 10 and 11). Furthermore, currently it is commonly supplied as an experimental tissue hypoxia detection kit (Non-patent Document 12).

As known attempts to detect a hypoxic region in vivo, compounds having a 2-nitroimidazole skeleton have been labeled with various radioactive nucleides and subjected to, for example, single-photon emission computed tomography (SPECT) (Non-patent Documents 13 to 16) or positron emission tomography (PET) employing [$^{18}$F]fluoromisonidazole ([$^{18}$F]FMISO), which is a radioactive fluorine-labeled misonidazole derivative (Non-patent Document 17).

Furthermore, as known radioactive fluorine-labeled compounds having a 2-nitroimidazole skeleton, there are [$^{18}$F]fluoroetanidazole ([$^{18}$F]FETA) (Non-patent Document 18), [$^{18}$F]fluoroerythronitroimidazole ([$^{18}$F]FETNIM) (Patent Document 3, Non-patent Document 19), 2-(2-nitro-1H-imidazol-1-yl)-N-(3-[$^{18}$F]fluoropropyl)-acetamide ([$^{18}$F]EF1) (Patent Document 4, Non-patent Document 20), 2-(2-nitro-1H-imidazol-1-yl)-N-(2,2,3,3-[$^{18}$F]pentafluoropropyl)-acetamide ([$^{18}$F]EF5) (Patent Document 5, Non-patent Document 21), [$^{18}$F]fluoroazomycinarabinofuranoside ([$^{18}$F]FAZA) (Non-patent Document 22, Non-patent Document 23), 4-bromo-1-(3-[$^{18}$F]fluoropropyl)-2-nitroimidazole (4-Br-[$^{18}$F]FPN) (Non-patent Document 24), etc.

RELATED DOCUMENTS

Patent Documents

[Patent Document 1] U.S. Pat. No. 5,674,693
[Patent Document 2] U.S. Pat. No. 5,086,068
[Patent Document 3] U.S. Pat. No. 5,728,843
[Patent Document 4] U.S. Pat. No. 6,252,087
[Patent Document 5] U.S. Pat. No. 7,230,115

Non-Patent Documents

[Non-patent Document 1] Thomlinson R H and Gray L H, "The histological structure of some human lung cancers and the possible implications for radiotherapy", Br J Cancer. December 9 (4): 539-49, 1955

[Non-patent Document 2] Kennedy K A et al., "The hypoxic tumor cell: a target for selective cancer chemotherapy", Biochem Pharmacol. January 1; 29 (1): 1-8, 1980

[Non-patent Document 3] Brizel D M et al., "Tumor hypoxia adversely affects the prognosis of carcinoma of the head and neck", Int J Radiat Oncol Biol Phys May 1; 38: 285-289, 1997

[Non-patent Document 4] Hockel M et al., "Intratumoral pO$_2$ predicts survival in advanced cancer of the uterine cervix", Radiother Oncol 26 (1): 45-50, 1993

[Non-patent Document 5] Nordsmark M, Overgaard M, Overgaard J "Pretreatment oxygenation predicts radiation response in advanced squamous cell carcinoma of the head and neck" Radiother Oncol 41: 31-39, 1996

[Non-patent Document 6] Brizel D M et al., "Tumor oxygenation predicts for the likelihood of distant metastases in human soft tissue sarcoma", Cancer Res. March 1; 56 (5): 941-3, 1996

[Non-patent Document 7] Suzuki Y et al., "Oxygenated and reoxygenated tumors show better local control in radiation therapy for cervical cancer", Int J Gynecol Cancer, January-February; 16 (1): 306-11, 2006

[Non-patent Document 8] Varghese A J et al., "Hypoxia-dependent reduction of 1-(2-nitro-1-imidazolyl)-3-methoxy-2-propanol by Chinese hamster ovary cells and KHT tumor cells in vitro and in vivo", Cancer Res. 36: 3761-3765, 1976

[Non-patent Document 9] Pettersen E O, "Toxic and Radiosensitizing Effect of the 2-Nitroimidazole Misonidazole (Ro-07-0582) on Murine CFU in vivo", Br. J. Cancer, 37, Suppl. III, 107-110, 1978

[Non-patent Document 10] Durand R E and Raleigh J A "Identification of nonproliferating but viable hypoxic tumor cells in vivo", Cancer Res 58: 3547-3550, 1998

[Non-patent Document 11] Nordsmark M et al., "Measurements of hypoxia using pimonidazole and polarographic oxygen-sensitive electrodes in human cervix carcinomas", Radiotherapy and Oncology; 67 (1), p 35-44, 2003

[Non-patent Document 12] Hypoxyprobe™ [online], Cosmo Bio Co., Ltd., 2011 [retrieved 28 Jun. 2011], internet <URL: http://www.cosmobio.co.jp/product/signal/cat41/cat93/00220001.asp?ent ry_id=1465>

[Non-patent Document 13] Urtasun R C et al., "Measurement of hypoxia in human tumours by non-invasive spect imaging of iodoazomycin arabinoside", Br J Cancer Suppl. July; 27: S209-S212, 1996

[Non-patent Document 14] Iyer R V et al., "A dual hypoxic marker technique for measuring oxygenation change within individual tumors", Br J Cancer. July; 78 (2): 163-169, 1998

[Non-patent Document 15] Ballinger J R et al., "In Vitro and In Vivo Evaluation of a Technetium-99m-Labeled 2-Nitroimidazole (BMS181321) as a Marker of Tumor Hypoxia", J Nucl Med, 37: 1023-1031, 1996

[Non-patent Document 16] Strauss H W et al., "Nitroimidazoles for imaging hypoxic myocardium", J Nucl Cardiol., 2: 437-445, 1995

[Non-patent Document 17] Rasey J S et al., "Radiolabelled fluoromisonidazole as an imaging agent for tumor hypoxia", Int J Radiat Oncol Biol Phys, November; 17 (5): 985-991, 1989

[Non-patent Document 18] Rasey J S et al., "Characterization of [$^{18}$F]Fluoroetanidazole, a New Radiopharmaceutical for Detecting Tumor Hypoxia" J. Nucl. Med. 40: 1072-1079, 1999

[Non-patent Document 19] Yang D J et al., "Development of F-18-labeled fluoroerythronitroimidazole as a PET agent for imaging tumor hypoxia" Radiology 194: 795-800, 1995

[Non-patent Document 20] Evans et al., "Noninvasive Detection of Tumor Hypoxia Using the 2-Nitroimidazole [$^{18}$F] EF1", J. Nucl. Med. 41: 327-336, 2000

[Non-patent Document 21] Ziemer L et al., "Noninvasive imaging of tumor hypoxia in rats using the 2-nitroimidazole $^{18}$F-EF5", Eur. J. Nucl. Med. Mol. Imaging 30: 259-266, 2003

[Non-patent Document 22] Sorger D et al., "[$^{18}$F]fluoroazomycinarabinofuranoside ($^{18}$FAZA) and [$^{18}$F]Fluoromisonidazole ($^{18}$FMISO): a comparative study of their selective uptake in hypoxic cells and PET imaging in experimental rat tumors", Nucl. Med. Biol. 30: 317-326, 2003

[Non-patent Document 23] Piert M, et al., "Hypoxia-specific tumor imaging with $^{18}$F-fluoroazomycin arabinoside", J Nucl Med, January; 46 (1): 106-13, 2005

[Non-patent Document 24] Yamamoto F et al., "Synthesis and Evaluation of 4-Bromo-1-(3-[8F]fluoropropyl)-2-nitroimidazole with a Low Energy LUMO Orbital Designed as Brain Hypoxia-Targeting Imaging Agent", Biol. Pharm. Bull. 25: 616-621

SUMMARY

However, in accordance with the knowledge of the present inventors, it has become clear that there is insufficient correlation between the intensity of accumulation of [$^{18}$F]FMISO in vivo and the concentration gradient of a hypoxic region detected by pimonidazole.

Because of this, the present inventors consider that there is still room for improvement in terms of the precision of in vivo quantitative evaluation of a hypoxic region by PET using a radioactive fluorine-labeled compound.

Non-patent Document 18 discloses an example in which oxygen concentration and accumulation of [$^{18}$F]FETA were examined using various types of tumor cells, but a correlation between tracer accumulation and oxygen concentration in vivo was not evaluated. Furthermore, Patent Documents 3 to 5 and Non-patent Documents 19 to 24 do not disclose a technique that focuses on a correlation between tracer accumulation and oxygen concentration in a hypoxic region.

The present invention has been accomplished in light of the above circumstances, and it is an object thereof to provide a radioactive fluorine-labeled compound that enables an in vivo hypoxic region to be quantitatively evaluated with good precision.

The present invention provides a compound represented by the following formula (1) or a salt thereof.

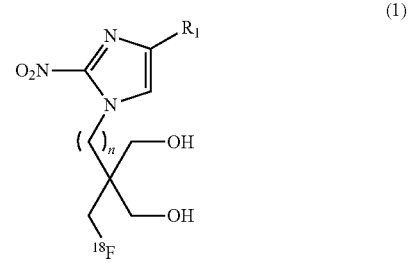

In the formula (1), $R_1$ denotes a hydrogen atom, a methyl group, or a hydroxymethyl group, and n is an integer of 1 or 2.

Furthermore, the present invention provides a compound represented by the following formula (2) or a salt thereof.

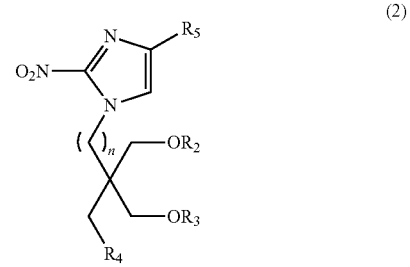

In the formula (2), $R_2$ and $R_3$ denote the same or mutually different hydroxy protecting groups, or $R_2$ and $R_3$ together denote a diol protecting group, $R_4$ denotes a non-radioactive halogen, a trialkylammonium having 3 to 12 carbon atoms, a straight-chain or branched alkylsulfonyloxy group having 1 to 10 carbon atoms, a straight-chain or branched haloalkylsulfonyloxy group having 1 to 10 carbon atoms, a substituted or unsubstituted arylsulfonyloxy group, or a dialkylsulfonium having 2 to 8 carbon atoms, $R_5$ denotes a hydrogen atom, a methyl group, or —$CH_2OR_6$, $R_6$ denotes a hydroxy protecting group, and n is an integer of 1 or 2.

Furthermore, the present invention provides a radioactive pharmaceutical composition containing a compound represented by the formula (1) or a salt thereof.

Moreover, the present invention provides a method of producing a compound represented by the formula (1) or a salt thereof from a compound represented by the formula (2) or a salt thereof.

Furthermore, the present invention provides an apparatus for producing a compound represented by the formula (1) or a salt thereof from a compound represented by the formula (2) or a salt thereof.

In accordance with the present invention, there can be provided a radioactive fluorine-labeled compound that enables an in vivo hypoxic region to be quantitatively evaluated with good precision.

BRIEF DESCRIPTION OF THE DRAWINGS

The above-mentioned object, other objects, features, and advantages will become apparent from preferred embodiments described below and their accompanying drawings below.

FIG. 15(a) is a diagram showing an immunohistochemical staining image.

DESCRIPTION OF EMBODIMENTS

Figure 1:
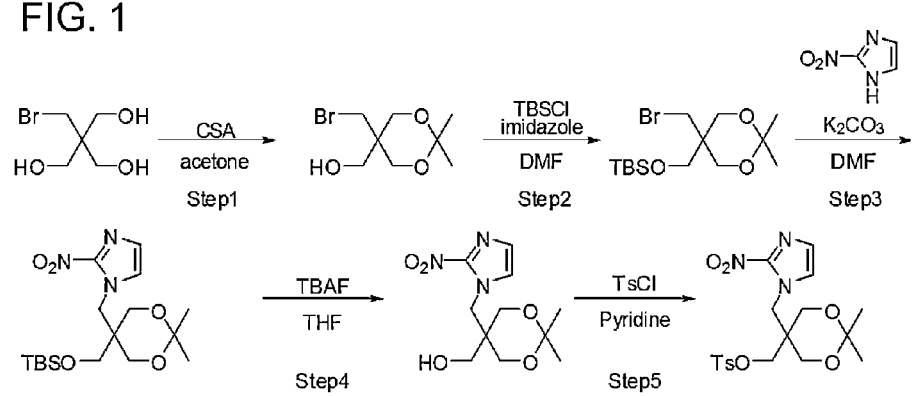
FIG. 1 is a synthetic scheme for 2,2-dimethyl-5-[(2-nitro-1H-imidazol-1-yl)methyl]-5-(p-toluenesulfonyloxymethyl)-1,3-dioxane.

Modes for carrying out the present invention are explained below.

The radioactive fluorine-labeled compound related to the present invention, as described above, is a compound represented by the formula (1) or a salt thereof, and in accordance with particularly preferred embodiments, it may be for example 1-(2,2-dihydroxymethyl-3-[$^{18}$F]fluoropropyl)-2-nitroimidazole, which is represented by the following formula (4), 1-(2,2-dihydroxymethyl-3-[$^{18}$F]fluoropropyl)-4-hydroxymethyl-2-nitroimidazole, which is represented by the following formula (5), or 1-(3,3-dihydroxymethyl-4-[$^{18}$F]fluorobutyl)-2-nitroimidazole, which is represented by the following formula (6).

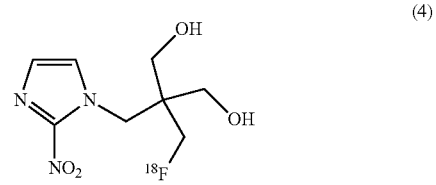

(4)

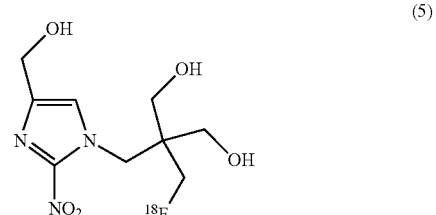

(5)

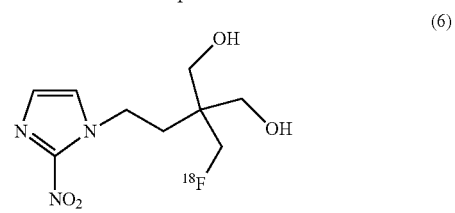

(6)

With regard to the radioactive fluorine-labeled compound related to the present invention, there is a case in which a compound represented by the formula (1) forms a salt, and such a salt may be included in the present invention as long as it is a pharmaceutically acceptable salt. Specific examples of the salt include an inorganic salt with hydrochloric acid, hydrobromic acid, hydroiodic acid, sulfuric acid, nitric acid, phosphoric acid, etc. and a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, or glutamic acid.

The radioactive fluorine-labeled compound related to the present invention may be produced using a compound represented by the formula (2) or a salt thereof as a labeling precursor. In the present specification, the 'labeling precursor' is a compound that is a starting material in a step of introducing fluorine 18, which is a radioactive isotope.

In the formula (2) $R_2$ and $R_3$ denote the same or mutually different hydroxy protecting groups, or $R_2$ and $R_3$ together denote a diol protecting group. As the hydroxy protecting group and the diol protecting group, those described in Greene's Protective Groups in Organic Synthesis, p. 17-245 (Wiley-Interscience; 4th edition) may be used.

When $R_2$ and $R_3$ independently denote the same or mutually different hydroxy protecting groups, $R_2$ and $R_3$ may preferably be selected from the group consisting of a trityl group, a monomethoxytrityl group, a dimethoxytrityl group, a trimethoxytrityl group, a methoxymethyl group, a 1-ethoxyethyl group, a methoxyethoxymethyl group, a benzyl group, a p-methoxybenzyl group, a 2-tetrahydropyranyl group, a trimethylsilyl group, a triethylsilyl group, a t-butyldimethylsilyl group, a t-butyldiphenylsilyl group, an acetyl group, a propanoyl group, a pivaloyl group, a palmitoyl group, a dimethylaminomethylcarbonyl group, an alanyl group, a 2,2,2-trichloroethoxycarbonyl group, a benzoyl group, and an allyloxycarbonyl group.

Furthermore, in the formula (2), when $R_2$ and $R_3$ together denote a diol protecting group $R_2$ and $R_3$ together denote for example a methylene group [—$CH_2$—], a 1-methylethan-1,1-diyl group [—$C(CH_3)_2$—], an ethan-1,1-diyl group [—CH($CH_3$)—], or a 1-phenylmethan-1,1-diyl group [—CHPh] and, as a result, may form a 1,3-dioxane ring. Among them, $R_2$ and $R_3$ are particularly preferably an acetonide group.

In the formula (2), $R_4$ is not particularly limited as long as it is a functional group that can undergo a nucleophilic substitution reaction, and is a non-radioactive halogen atom, a trialkylammonium having 3 to 12 carbon atoms, a straight-chain or branched alkylsulfonyloxy group having 1 to 10 carbon atoms, a straight-chain or branched haloalkylsulfonyloxy group having 1 to 10 carbon atoms, a substituted or unsubstituted arylsulfonyloxy group, or a dialkylsulfonium having 2 to 8 carbon atoms.

Examples of the non-radioactive halogen atom include a fluorine atom, a chlorine atom, a bromine atom, and an iodine atom, and a bromine atom or an iodine atom is preferable.

The trialkylammonium having 3 to 12 carbon atoms is represented by —$N^+(R_{11})(R_{12})(R_{13})X_a^-$. $R_{11}$, $R_{12}$, and $R_{13}$ are mutually independently selected from the group consisting of substituted or unsubstituted alkyl, may be straight-chain alkyl or branched alkyl, and are preferably straight-chain unsubstituted alkyl. Among them, trimethylammonium or triethylammonium is preferable. $X_a^-$ may be an organic acid anion such as $CF_3S(O)_2O^-$, $C_4F_9S(O)_2O^-$, or trifluoroacetic acid anion ($CF_3$—$C(O)O^-$) or an inorganic acid anion such as iodide anion, bromide anion, chloride anion, perchlorate anion ($ClO_4^-$), or phosphate anion.

Examples of the straight-chain or branched alkylsulfonyloxy group having 1 to 10 carbon atoms include a methanesulfonyloxy group and an ethanesulfonyloxy group.

Examples of the straight-chain or branched haloalkylsulfonyloxy group having 1 to 10 carbon atoms include a trifluoromethanesulfonyloxy group.

Examples of the arylsulfonyloxy group include an arylsulfonyloxy group having 6 to 10 carbon atoms, such as a benzenesulfonyloxy group or a naphthalenesulfonyloxy group. Examples of a group with which these arylsulfonyloxy groups may be substituted include an optionally substituted alkyl group such as a methyl group, an ethyl group, a n-propyl group, an isopropyl group, a n-butyl group, an isobutyl group, a sec-butyl group, a tert-butyl group, or a n-pentyl group; a halogen atom such as a fluorine atom, a chlorine atom, or a bromine atom; an alkoxy group such as a methoxy group or an ethoxy group; an alkylcarbonyl group such as an acetyl group or a propionyl group; and a nitro group. Specific examples of an alkylsulfonyloxy group substituted with such a group include a p-toluenesulfonyloxy group and a 2-nitrobenzenesulfonyloxy group.

The dialkylsulfonium having 2 to 8 carbon atoms is represented by —$S^+(R_{14})(R_{15})X_b^-$. $R_{14}$ and $R_{15}$ are mutually independently selected from the group consisting of substituted or unsubstituted alkyls, may be straight-chain alkyl or branched alkyl, and are preferably straight-chain unsubstituted alkyls. Among them, dimethylsulfonium or diethylsulfonium is preferable. $X_b^-$ may be an organic acid anion such as $CF_3S(O)_2O^-$, $C_4F_9S(O)_2O^-$, or trifluoroacetic acid anion ($CF_3$—$C(O)O^-$), or an inorganic acid anion such as iodide anion, bromide anion, chloride anion, perchloric acid anion ($ClO_4^-$), or phosphate anion.

In the formula (2), $R_4$ is preferably a non-radioactive bromine atom or iodine atom, a p-toluenesulfonyloxy group, a trifluoromethylsulfonyloxy group, a methanesulfonyloxy group, or a 2-nitrobenzenesulfonyloxy group. Among them, a non-radioactive bromine atom or iodine atom or a p-toluenesulfonyloxy group are particularly preferable.

In the formula (2), $R_5$ denotes a hydrogen atom, a methyl group, or —$CH_2OR_6$. $R_6$ is not particularly limited as long as it is a protecting group used for a hydroxy group; those described in Greene's Protective Groups in Organic Synthesis, p. 17-245 (Wiley-Interscience; 4th edition) may be used. A trityl group, a monomethoxytrityl group, a dimethoxytrityl group, a trimethoxytrityl group, a methoxymethyl group, a 1-ethoxyethyl group, a methoxyethoxymethyl group, a benzyl group, a p-methoxybenzyl group, a 2-tetrahydropyranyl group, a trimethylsilyl group, a triethylsilyl group, a t-butyldimethylsilyl group, a t-butyldiphenylsilyl group, an acetyl group, a propanoyl group, a pivaloyl group, a palmitoyl group, a dimethylaminomethylcarbonyl group, an alanyl group, a 2,2,2-trichloroethoxycarbonyl group, a benzoyl group, an allyloxycarbonyl group, etc. may preferably be used.

When $R_2$ and $R_3$ independently denote the same or mutually different hydroxy protecting groups, $R_2$, $R_3$, and $R_6$ may be the same hydroxy protecting group or may be mutually different hydroxy protecting groups.

A method for synthesizing a labeling precursor for the radioactive fluorine-labeled compound related to the present invention is explained below with 2,2-dimethyl-5-[(2-nitro-1H-imidazol-1-yl)methyl]-5-(p-toluenesulfonyloxymethyl)-1,3-dioxane as an example.

The synthetic scheme for 2,2-dimethyl-5-[(2-nitro-1H-imidazol-1-yl)methyl]-5-(p-toluenesulfonyloxymethyl)-1,3-dioxane is shown in FIG. 1. When synthesizing 2,2-dimethyl-5-[(2-nitro-1H-imidazol-1-yl)methyl]-5-(p-toluenesulfonyloxymethyl)-1,3-dioxane, a protecting group is first introduced to two hydroxy groups of 2-bromomethyl-2-hydroxymethyl-1,3-propanediol. As the protecting group used here, one that does not exhibit reactivity under neutral or basic conditions but is easily removed by deprotection under acidic conditions may be used. In a preferred embodiment, 2-bromomethyl-2-hydroxymethyl-1,3-propanediol and acetone are reacted with an acid as a catalyst to thus prepare 5-bromomethyl-2,2-dimethyl-5-hydroxymethyl-1,3-dioxane, in which the protecting group is introduced on the diol (FIG. 1, Step 1). As the acid catalyst used here, various acids that do not exhibit reactivity toward these starting material compounds may be used. Typically, an acid such as 10-camphorsulfonic acid, sulfuric acid, or p-toluenesulfonic acid may be used, and 10-camphorsulfonic acid may preferably be used. This step may be carried out by for example a method of Piganiol, P et al. (Bulletin de la Societe Chimique de France, 1959, p. 1860-1863).

Subsequently, a protecting group is introduced on the hydroxy group of the obtained 5-bromomethyl-2,2-dimethyl-5-hydroxymethyl-1,3-dioxane (FIG. 1, Step 2), and then 2-nitroimidazole is introduced by a substitution reaction of the bromine atom of the bromomethyl group (FIG. 1, Step 3).

As the hydroxy protecting group in this case, various types of protecting groups normally used as a hydroxy protecting group may be used, but it is necessary to use one that does not require acidic conditions for deprotection. In a preferred embodiment, a t-butyldimethylsilyl group may be used as the protecting group. Introduction of a t-butyldimethylsilyl group may be carried out by for example a method of E. J. Corey et al. (Journal of American Chemical Society, 1972, 94, p. 6190).

Furthermore, introduction of 2-nitroimidazole into the bromomethyl group may be carried out by for example a method of Hay, Michael P et al. (Journal of Medicinal Chemistry, 1995, 38 (11), p. 1928-41).

Subsequently, the obtained 5-(t-butyldimethylsiloxymethyl)-2,2-dimethyl-5-[(2-nitro-1H-imidazol-1-yl)methyl]-1,3-dioxane is reacted with tetra-n-butylammonium fluoride in an organic solvent by for example a method of E. J. Corey et al. (Journal of American Chemical Society, 1972, 94, p. 6190) and purified, to give 2,2-dimethyl-5-hydroxymethyl-5-[(2-nitro-1H-imidazol-1-yl)methyl]-1,3-dioxane (FIG. 1, Step 4).

The obtained 2,2-dimethyl-5-hydroxymethyl-5-[(2-nitro-1H-imidazol-1-yl)methyl]-1,3-dioxane is reacted with p-toluenesulfonyl chloride by for example a method of L. F. Fieser et al. (Reagents for Organic Synthesis, Vol. 1, Wiley, New York, p. 1179 (1967)) and purified, to give the desired 2,2-dimethyl-5-[(2-nitro-1H-imidazol-1-yl)methyl]-5-(p-toluenesulfonyloxymethyl)-1,3-dioxane (FIG. 1, Step 5).

In addition, when synthesizing 2,2-dimethyl-5-[(2-nitro-1H-imidazol-1-yl)methyl]-5-(p-toluenesulfonyloxymethyl)-1,3-dioxane, each of protecting groups may be introduced to the respective hydroxy groups of the diol, or one protecting group may be introduced for the two hydroxy groups.

When it is obtained a compound in which the hydroxymethyl group at the 5-position of the dioxane ring of 2,2-dimethyl-5-hydroxymethyl-5-[(2-nitro-1H-imidazol-1-yl) methyl]-1,3-dioxane is substituted with a substituent other than a p-toluenesulfonyloxy group, that is, a compound represented by in the formula (2) in which $R_4$ is a substituent other than a p-toluenesulfonyloxy group, various reagents instead of the p-toluenesulfonyl chloride for any purpose, in Step 5 of FIG. 1 may be used in an appropriate solvent. For example, when a compound represented by the formula (2) in which $R_4$ is a trifluoromethylsulfonyloxy group is obtained, trifluoromethanesulfonic acid anhydride may be used. Furthermore, when $R_4$ in the formula (2) is a methylsulfonyloxy group, methylsulfonyl chloride may be used.

The labeling precursor for the radioactive fluorine-labeled compound related to the present invention may be synthesized by combining known reactions using generally available starting materials without being limited to the above examples. For example, a compound represented by the formula (2) in which $R_2$ and $R_3$ are oxygens bonded to a 1-methylethan-1,1-diyl group, $R_4$ is a p-toluenesulfonyloxy group, $R_6$ is a methoxymethoxymethyl group, and n is 1 may be synthesized in accordance with the steps of FIG. 1 above by adding a reaction of replacing a hydrogen atom at the 4-position of the imidazole skeleton with a hydroxymethyl group after Step 3 of FIG. 1.

In addition, the labeling precursor of the radioactive fluorine-labeled compound related to the present invention can include a case in which a compound represented by the formula (2) forms a salt. Specific examples of the salt include an inorganic salt such as hydrochloric acid, hydrobromic acid, hydroiodic acid, sulfuric acid, nitric acid or phosphoric acid, and an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid or glutamic acid.

As a method of synthesizing a radioactive fluorine-labeled compound related to the present invention using the obtained labeling precursor, for example, there can be cited a method of synthesizing a compound represented by the formula (1) or a salt thereof by reacting [$^{18}$F]fluoride ion which has been obtained by a known method in the presence of a base to synthesize a compound represented by the following formula (3) or a salt thereof from a compound represented by the formula (2) or a salt thereof, and then deprotecting the mutually independent hydroxy protecting groups or the diol protecting group for $R_2$ and $R_3$ in the formula (3).

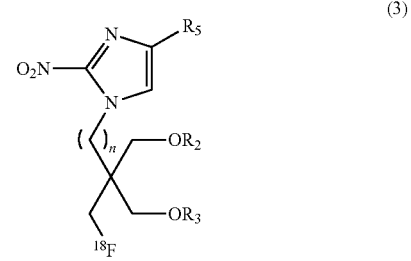

(3)

In the formula (3), $R_2$ and $R_3$ denote the same or mutually different hydroxy protecting groups, or $R_2$ and $R_3$ together denote a diol protecting group, $R_5$ denotes a hydrogen atom, a methyl group, or —$CH_2OR_6$, $R_6$ denotes a hydroxy protecting group, and n is an integer of 1 or 2.

The compound of the formula (3) is preferably obtained by carrying out reaction at a temperature of 20° C. to 120° C. using an [$^{18}$F]fluoride ion aqueous solution produced as the [$^{18}$F]fluoride ion from [$^{18}$O] water by means of a cyclotron, and an base such as a tetrabutylammonium or potassium carbonate/Kryptofix 222, in an appropriate solvent such as an aprotic solvent like acetonitrile, N,N-dimethylformamide or dimethylsulfoxide.

The hydroxy protecting groups or diol protecting group denoted by $R_2$, $R_3$ and $R_6$ may be removed by a known method.

Production steps of obtaining the radioactive fluorine-labeled compound related to the present invention from a compound represented by the formula (2) or a salt thereof may be carried out using for example a synthetic apparatus equipped with a reaction container and a shielding body. Furthermore, this synthetic apparatus may be an automated synthetic apparatus for which all the steps are automated.

In the present invention, a radioactive pharmaceutical composition may also be prepared from the produced radioactive fluorine-labeled compound. In the present specification, the 'radioactive pharmaceutical composition' may be defined as a formulation preparation that contains a compound represented by the formula (1) or a salt thereof in a form that is suitable for administration into a living body. This radioactive pharmaceutical composition is preferably administered parenterally, that is, via injection, and is more preferably an aqueous solution. Such a composition may contain as appropriate an additional component such as a pH-adjusting agent or a pharmaceutically acceptable solubilizing agent, stabilizer, or antioxidant.

A hypoxic region may be imaged by introducing the radioactive fluorine-labeled compound related to the present invention into an organism, and detecting radioactivity using a radiation detector, a positron emission tomography scanner, autoradiography, etc.

It becomes possible to detect an in vivo hypoxic region noninvasively by administering the radioactive fluorine-labeled compound related to the present invention into a living body, and detecting radioactivity using a general-purpose PET apparatus. Furthermore, since the radioactive fluorine-labeled compound related to the present invention has a structure represented by the formula (1), it is quickly washed out from normal tissue while having affinity for an in vivo hypoxic region. It is therefore possible to obtain a hypoxic region diagnostic agent having an excellent ability to image an in vivo hypoxic region.

Moreover, since the uptake of the radioactive fluorine-labeled compound related to the present invention into an organ other than a tumor, such as the liver due to lipid solubility of a compound, is low, the ratio of tumor to normal tissue is high. Therefore, the radioactive fluorine-labeled compound related to the present invention can preferably be used in imaging of a hypoxic region of a tumor, and is useful also as a tumor diagnostic agent.

EXAMPLES

The present invention is explained below in further detail by reference to the Examples, but the present invention should not be construed as being limited to the contents thereof. In the following Examples, the names of compounds provided to experiments are as defined in Table 1.

TABLE 1

| Compound name | Common Name |
| --- | --- |
| Compound 1 | 1-(2,2-Dihydroxymethyl-3-[$^{18}$F]fluoropropyl)-2-nitroimidazole |
| Compound 2 | 1-(2,2-Dihydroxymethyl-3-[$^{18}$F]fluoropropyl)-4-hydroxymethyl-2-nitroimidazole |
| Compound 3 | 1-(3,3-Dihydroxymethyl-4-[$^{18}$F]fluorobutyl)-2-nitroimidazole |

In the Examples, analysis and purification of each compound were carried out as follows.

1. Determination of Molecular Structure of Non-Radioactive Compound by NMR Spectroscopy In the Examples, the structure of a non-radioactive compound was identified by NMR spectroscopy. An NMR spectrum was obtained using a JNM-ECP-500 (manufactured by JEOL) as an NMR spectrometer. The resonance frequency was 500 MHz for $^1$H-NMR and 470 MHz for $^{19}$F-NMR. For $^1$H-NMR, a residual solvent signal in a deuterated solvent was used as a reference (DMSO-d: δ2.5; CD$_3$OD δ3.3; CDCl$_3$ δ7.26). All chemical shifts are expressed as ppm on the delta scale (δ), and fine splitting of a signal is expressed using abbreviations (s: singlet, d: doublet, t: triplet, dt: double triplet, m: multiplet, brs: broad singlet).

2. Identification and Purification of Compounds 1 to 3 by HPLC Chromatography
Column: CAPCELL PAK (trade name, Shiseido, size: 10 mmø×250 mm)

Detector: UV-visible absorptiometer (detection wavelength: 280 nm)

3. Measurement of Radiochemical Purity of Compounds 1 to 3 by TLC Analysis
TLC plate: Silica Gel 60 F$_{254}$ (product name; manufactured by Merck)
Development phase: ethyl acetate
Detector: Rita Star (product name; manufactured by raytest)

Example 1

Production of 2,2-dimethyl-5-[(2-nitro-1H-imidazol-1-yl)methyl]-5-(p-toluenesulfonyloxymethyl)-1,3-dioxane 2,2-Dimethyl-5-[(2-nitro-1H-imidazol-1-yl)methyl]-5-(p-toluenesulfonyloxymethyl)-1,3-dioxane) is a labeling precursor for compound 1. FIG. 1 shows the synthetic scheme therefor.

Synthesis of 5-bromomethyl-2,2-dimethyl-5-hydroxymethyl-1,3-dioxane (FIG. 1, Step 1)

423 mg (2.13 mmol equivalents) of 2-bromomethyl-2-hydroxymethyl-1,3-propanediol was dissolved in 1.0 mL of acetone, 247 mg (1.07 mmol equivalents) of 10-camphorsulfonic acid was added thereto, and the mixture was stirred at room temperature (25° C.) for 2 days. After completion of the reaction, triethylamine was added, the solvent was removed by distillation, and the obtained crude product was then purified by silica gel column chromatography (eluent: hexane/ethyl acetate (v/v)=3/1) to give 409 mg (1.71 mmol equivalents) of 5-bromomethyl-2,2-dimethyl-5-hydroxymethyl-1,3-dioxane.

$^1$H-NMR (solvent: deuterated chloroform) of 5-bromomethyl-2,2-dimethyl-5-hydroxymethyl-1,3-dioxane: δ 3.79-3.74 (m, 4H), 3.71 (d, J=5.5 Hz, 2H), 3.56 (s, 2H), 1.59 (t, J=5.5 Hz, 1H), 1.41 (s, 3H), 1.41 (s, 3H).

Synthesis of 5-bromomethyl-5-(t-butyldimethylsiloxymethyl)-2,2-dimethyl-1,3-dioxane (FIG. 1, Step 2)

409 mg (1.71 mmol equivalents) of 5-bromomethyl-2,2-dimethyl-5-hydroxymethyl-1,3-dioxane was dissolved in 5 mL of dimethylformamide, 233 mg (3.42 mmol equivalents) of imidazole and 309 mg (2.05 mmol equivalents) of t-butyldimethylchlorosilane were added thereto, and the mixture was stirred at room temperature (25° C.) for 18 hours. After completion of the reaction, a saturated aqueous solution of ammonium chloride and water were added thereto, and the mixture was extracted three times with ethyl acetate. The combined ethyl acetate layers were washed with water and brine, then dried with anhydrous magnesium sulfate and subsequently concentrated under vacuum, and the obtained crude product was purified by silica gel column chromatography (eluent: hexane/ethyl acetate (v/v)=20/1) to give 578 mg (1.64 mmol equivalents) of 5-bromomethyl-5-(t-butyldimethylsiloxymethyl)-2,2-dimethyl-1,3-dioxane.

$^1$H-NMR (solvent: deuterated chloroform) of 5-bromomethyl-5-(t-butyldimethylsiloxymethyl)-2,2-dimethyl-1,3-dioxane: δ 3.78-3.70 (m, 4H), 3.59 (s, 2H), 3.54 (s, 2H), 1.40 (s, 3H), 1.40 (s, 3H), 0.89 (s, 9H), 0.06 (s, 6H).

Synthesis of 5-(t-butyldimethylsiloxymethyl)-2,2-dimethyl-5-[(2-nitro-1H-imidazol-1-yl)methyl]-1,3-dioxane (FIG. 1, Step 3)

578 mg (1.64 mmol equivalents) of 5-bromomethyl-5-(t-butyldimethylsiloxymethyl)-2,2-dimethyl-1,3-dioxane was dissolved in 10 mL of dimethylformamide, 186 mg (1.64 mmol equivalents) of 2-nitroimidazole and 680 mg (4.92 mmol equivalents) of potassium carbonate were added thereto, and the mixture was heated to 100° C. for 18 hours. After completion of the reaction, the reaction liquid was cooled to room temperature (25° C.), a saturated aqueous solution of ammonium chloride and water were added thereto, and the mixture was extracted three times with ethyl acetate. The combined ethyl acetate layers were washed with water and brine, then dried with anhydrous magnesium sulfate and subsequently concentrated under vacuum, and the obtained crude product was purified by silica gel column chromatography (eluent: hexane/ethyl acetate (v/v)=3/1) to give 363 mg (0.942 mmol equivalents) of 5-(t-butyldimethylsiloxymethyl)-2,2-dimethyl-5-[(2-nitro-1H-imidazol-1-yl)methyl]-1,3-dioxane.

$^1$H-NMR (solvent: deuterated dimethylsulfoxide) of 5-(t-butyldimethylsiloxymethyl)-2,2-dimethyl-5-[(2-nitro-1H-imidazol-1-yl)methyl]-1,3-dioxane: δ 7.21 (d, J=1.1 Hz, 1H), 7.13 (d, J=1.1 Hz, 1H), 4.74 (s, 2H), 3.74 (d, J=12.4 Hz, 2H), 3.56 (d, J=12.4 Hz, 2H), 3.48 (s, 2H), 1.42 (s, 3H), 1.42 (s, 3H), 0.88 (s, 9H), 0.04 (s, 6H).

Synthesis of 2,2-dimethyl-5-hydroxymethyl-5-[(2-nitro-1H-imidazol-1-yl)methyl]-1,3-dioxane (FIG. 1, Step 4)

363 mg (0.942 mmol equivalents) of 5-(t-butyldimethylsiloxymethyl)-2,2-dimethyl-5-[(2-nitro-1H-imidazol-1-yl)methyl]-1,3-dioxane was dissolved in 10.0 mL of tetrahydrofuran, 0.94 mL (1.0 mol/L solution, 0.94 mmol equivalents) of a tetrahydrofuran solution of tetrabutylammonium fluoride was added thereto, and the mixture was stirred at room temperature (25° C.) for 10 minutes. After completion of the reaction, a saturated aqueous solution of ammonium chloride and water were added thereto, and the mixture was extracted three times with ethyl acetate. The combined ethyl acetate layers were washed with water and brine, then dried with anhydrous magnesium sulfate and subsequently concentrated under vacuum, and the obtained crude product was purified by silica gel column chromatography (eluent: hexane/ethyl acetate (v/v)=1/3) to give 221 mg (0.815 mmol equivalents) of 2,2-dimethyl-5-hydroxymethyl-5-[(2-nitro-1H-imidazol-1-yl)methyl]-1,3-dioxane.

$^1$H-NMR (solvent: deuterated chloroform) of 2,2-dimethyl-5-hydroxymethyl-5-[(2-nitro-1H-imidazol-1-yl)methyl]-1,3-dioxane: δ 7.31 (d, J=1.0 Hz, 1H), 7.15 (d, J=1.0 Hz, 1H), 4.82 (s, 2H), 3.78 (d, J=12.6 Hz, 2H), 3.58 (d, J=12.6 Hz, 2H), 3.48 (d, J=4.7 Hz, 2H), 1.72 (t, J=4.7 Hz, 1H), 1.46 (s, 3H), 1.45 (s, 3H).

Synthesis of 2,2-dimethyl-5-[(2-nitro-1H-imidazol-1-yl)methyl]-5-(p-toluenesulfonyloxymethyl)-1,3-dioxane (FIG. 1, Step 5)

100 mg (0.369 mmol equivalents) of 2,2-dimethyl-5-hydroxymethyl-5-[(2-nitro-1H-imidazol-1-yl)methyl]-1,3-dioxane was dissolved in 4.0 mL of pyridine and cooled to 0° C., 77.3 mg (0.406 mmol equivalents) of p-toluenesulfonyl chloride was then added thereto, and the mixture was stirred at room temperature (25° C.) for 1 hours. After completion of the reaction, a saturated aqueous solution of ammonium chloride and water were added thereto, and the mixture was extracted three times with ethyl acetate. The combined ethyl acetate layers were washed with water and brine, then dried with anhydrous magnesium sulfate and subsequently concentrated under vacuum, and the obtained crude product was purified by silica gel column chromatography (eluent: hexane/ethyl acetate (v/v)=1/1) to give 115 mg (0.270 mmol equivalents) of 2,2-dimethyl-5-[(2-nitro-1H-imidazol-1-yl)methyl]-5-(p-toluenesulfonyloxymethyl)-1,3-dioxane.

$^1$H-NMR (solvent: deuterated chloroform) of 2,2-dimethyl-5-[(2-nitro-1H-imidazol-1-yl)methyl]-5-(p-toluenesulfonyloxymethyl)-1,3-dioxane: δ 7.76 (d, J=8.3 Hz, 2H), 7.38 (d, J=8.3 Hz, 2H), 7.20 (s, 1H), 7.14 (s, 1H), 4.72 (s, 2H), 3.93 (s, 2H), 3.71 (d, J=12.4 Hz, 2H), 3.60 (d, J=12.4 Hz, 2H), 2.47 (s, 3H), 1.40 (s, 3H), 1.34 (s, 3H).

Example 2

Figure 2:
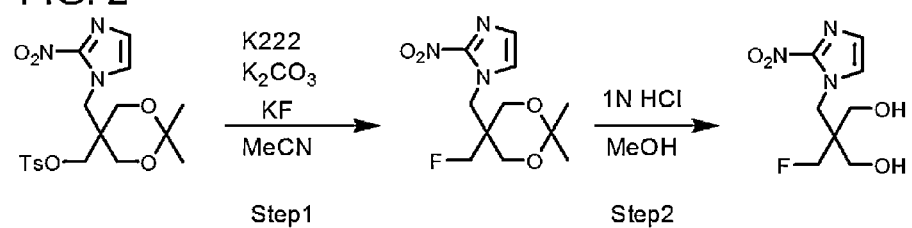
FIG. 2 is a synthetic scheme for 1-(2,2-dihydroxymethyl-3-fluoropropyl)-2-nitroimidazole.

Production of 1-(2,2-dihydroxymethyl-3-fluoropropyl)-2-nitroimidazole 1-(2,2-Dihydroxymethyl-3-fluoropropyl)-2-nitroimidazole is a compound (non-radioactive compound 1) having the same structure as that of compound 1 except that the fluorine atom of compound 1 is changed from fluorine 18 to fluorine 19. FIG. 2 shows the synthetic scheme therefor.

Synthesis of 2,2-dimethyl-5-fluoromethyl-5-[(2-nitro-1H-imidazol-1-yl)methyl]-1,3-dioxane (FIG. 2, Step 1)

30 mg (0.0705 mmol equivalents) of 2,2-dimethyl-5-[(2-nitro-1H-imidazol-1-yl)methyl]-5-(p-toluenesulfonyloxymethyl)-1,3-dioxane was dissolved in 1.0 mL of acetonitrile, 39.8 mg (0.106 mmol equivalents) of Kryptofix 222 (trade name, Merck), 5.1 mg (0.088 mmol equivalents) of potassium fluoride, and 2.0 mg (0.014 mmol equivalents) of potassium carbonate were added thereto, and the mixture was stirred under reflux by heating for 3 hours. After completion of the reaction, the reaction liquid was cooled to room temperature (25° C.), the solvent was then removed by distillation, and the obtained crude product was purified by silica gel column chromatography (eluent: hexane/ethyl acetate (v/v)=2/1) to give 9.2 mg (0.034 mmol equivalents) of 2,2-dimethyl-5-fluoromethyl-5-[(2-nitro-1H-imidazol-1-yl)methyl]-1,3-dioxane.

$^1$H-NMR (solvent: deuterated chloroform) of 2,2-dimethyl-5-fluoromethyl-5-[(2-nitro-1H-imidazol-1-yl)methyl]-1,3-dioxane: δ 7.23 (d, J=0.9 Hz, 1H), 7.18 (d, J=0.9 Hz, 1H), 4.80 (s, 2H), 4.36 (d, $J_{H-F}$=47.2 Hz, 2H), 3.83 (d, J=12.6 Hz, 2H), 3.64 (d, J=12.6 Hz, 2H), 1.45 (s, 3H), 1.44 (s, 3H).

The reaction of Step 1 shown in FIG. 2 was repeated so as to synthesize an amount of 2,2-dimethyl-5-fluoromethyl-5-[(2-nitro-1H-imidazol-1-yl)methyl]-1,3-dioxane sufficient to be used in the following step.

Synthesis of 1-(2,2-dihydroxymethyl-3-fluoropropyl)-2-nitroimidazole (FIG. 2, Step 2)

56.3 mg (0.206 mmol equivalents) of 2,2-dimethyl-5-fluoromethyl-5-[(2-nitro-1H-imidazol-1-yl)methyl]-1,3-dioxane was dissolved in 2 mL of methanol, 2 mL of 1 mol/L hydrochloric acid was added thereto, and the mixture was heated at 80° C. for 2 hours. After completion of the reaction, the reaction liquid was cooled to room temperature (25° C.), the solvent was then removed by distillation, and the obtained crude product was washed with ethyl acetate to give 47.3 mg (0.203 mmol equivalents) of 1-(2,2-dihydroxymethyl-3-fluoropropyl)-2-nitroimidazole (FIG. 2, Step 2).

$^1$H-NMR (solvent: deuterated chloroform) of 1-(2,2-dihydroxymethyl-3-fluoropropyl)-2-nitroimidazole: δ 7.33 (d, J=1.1 Hz, 1H), 7.15 (d, J=1.1 Hz, 1H), 4.76 (s, 2H), 4.41 (d, $J_{H-F}$=47.2 Hz, 2H), 3.69-3.68 (m, 4H).

Example 3

Production of 1-(2,2-dihydroxymethyl-3-[$^{18}$F]fluoropropyl)-2-nitroimidazole (Compound 1)

Figure 3:
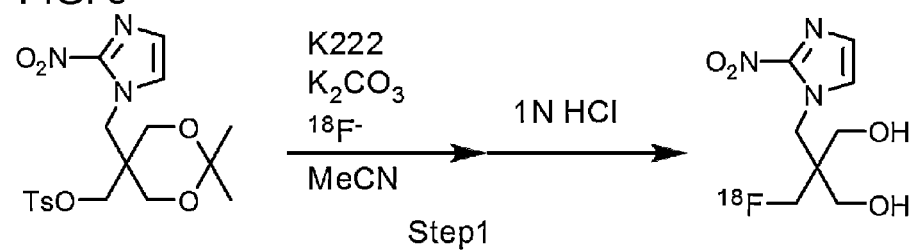
FIG. 3 is a synthetic scheme for 1-(2,2-dihydroxymethyl-3-[$^{18}$F]fluoropropyl)-2-nitroimidazole.

FIG. 3 shows the synthetic scheme therefor.

[$^{18}$F]Fluoride ion-containing H$_2$$^{18}$O (amount of radioactivity 1393 MBq, value corrected when synthesis started) was passed through an anion-exchange column (Sep-Pak (registered trademark) Accell Plus QMA Plus Light (trade name), manufactured by Nihon Waters K.K.) that had been pretreated with an aqueous solution of potassium carbonate to collect [$^{18}$F]fluoride ion by adsorption. Subsequently, an aqueous solution of potassium carbonate (42.4 µmol/L, 0.3 mL) and a solution of 14 mg (37.2 µmol equivalents) of Kryptofix 222 (trade name, Merck) in 0.7 mL of acetonitrile were passed through this column to elute [$^{18}$F]fluoride ion.

This eluate was heated under a flow of argon gas to 110° C. so as to evaporate water, acetonitrile (0.3 mL×2) was then added, and the mixture was subjected to azeotropic distillation to dryness. A solution of 5 mg (11.4 µmol equivalents) of 2,2-dimethyl-5-[(2-nitro-1H-imidazol-1-yl)methyl]-5-(p-toluenesulfonyloxymethyl)-1,3-dioxane synthesized in the Example 1 dissolved in 0.3 mL of acetonitrile was added thereto, and the mixture was heated at 110° C. for 10 minutes. Subsequently, 0.3 mL of 1 mol/L hydrochloric acid was added, and the mixture was heated at 110° C. for 3 minutes. After completion of the reaction, 1.0 mL of water was added, the mixture was subjected to HPLC (mobile phase: 0.1 (v/v) % trifluoroacetic acid aqueous solution/acetonitrile (containing 0.1 (v/v) % trifluoroacetic acid) (v/v)=85/15, flow rate: 4.0 mL/min) and identified using the non-radioactive compound 1 obtained in the Example 2 such that a peak at a retention time of 10 minutes was a fraction of compound 1, and the fraction of compound 1 thus identified was collected.

10 mL of water was added to this fraction, the liquid thus obtained was passed through a Sep-Pak (registered trademark) HLB Plas (trade name, manufactured by Nihon Waters K.K.), and compound 1 was collected on the column by absorption. This column was washed with 3 mL of water, and 2 mL of ethanol was then passed through to thus elute compound 1. The amount of radioactivity obtained was 388 MBq (69 minutes after start of synthesis). When TLC analysis was carried out, it was found that the radiochemical purity was 98%.

Example 4

Figure 4:
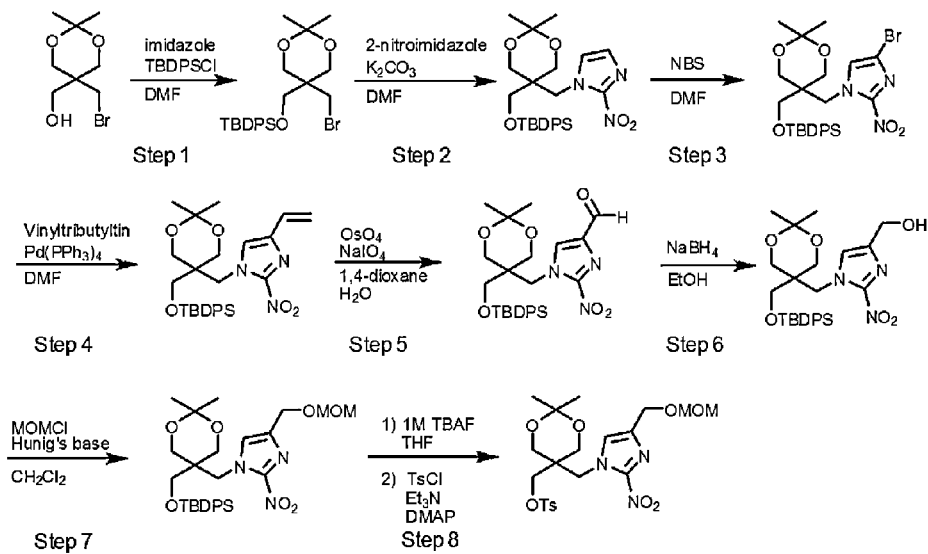
FIG. 4 is a synthetic scheme for 2,2-dimethyl-5-[(4-methoxymethoxymethyl-2-nitro-1H-imidazol-1-yl)methyl]-5-(p-toluenesulfonyloxymethyl)-1,3-dioxane.

Production of 2,2-dimethyl-5-[(4-methoxymethoxymethyl-2-nitro-1H-imidazol-1-yl)methyl]-5-(p-toluenesulfonyloxymethyl)-1,3-dioxane 2,2-Dimethyl-5-[(4-methoxymethoxymethyl-2-nitro-1H-imidazol-1-yl)methyl]-5-(p-toluenesulfonyloxymethyl)-1,3-dioxane is a labeling precursor for compound 2. FIG. 4 shows the synthetic scheme therefor.

Synthesis of 5-bromomethyl-5-(t-butyldiphenylsiloxymethyl)-2,2-dimethyl-1,3-dioxane (FIG. 4, Step 1)

1.1 g (4.6 mmol equivalents) of 5-bromomethyl-2,2-dimethyl-5-hydroxymethyl-1,3-dioxane was dissolved in 23 mL of dimethylformamide, 626 mg (9.2 mmol equivalents) of imidazole and 1.43 mL (5.5 mmol equivalents) of t-butyldiphenylsilane chloride were added thereto, and the mixture was stirred at room temperature (25° C.) for 5 hours. After completion of the reaction, a saturated aqueous solution of ammonium chloride was added dropwise, and the mixture was extracted with ethyl acetate three times. The combined ethyl acetate layers were washed with water and brine, then dried with anhydrous magnesium sulfate, and subsequently concentrated under vacuum. The obtained crude product was purified by silica gel column chromatography (eluent: hexane/ethyl acetate (v/v)=20/1) to give 1.70 g (3.56 mmol equivalents) of 5-bromomethyl-5-(t-butyldiphenylsiloxymethyl)-2,2-dimethyl-1,3-dioxane.

$^1$H-NMR (solvent: deuterated chloroform) of 5-bromomethyl-5-(t-butyldiphenylsiloxymethyl)-2,2-dimethyl-1,3-dioxane: δ 7.67-7.65 (m, 4H), 7.44-7.38 (m, 6H), 3.81 (d, J=11.9 Hz, 2H), 3.76 (d, J=11.9 Hz, 2H), 3.67 (s, 2H), 3.65 (s, 2H), 1.41 (s, 3H), 1.36 (s, 3H), 1.06 (s, 9H).

Synthesis of 5-(t-butyldiphenylsiloxymethyl)-2,2-dimethyl-5-[(2-nitro-1H-imidazol-1-yl)methyl]-1,3-dioxane (FIG. 4, Step 2)

1.70 g (3.56 mmol equivalents) of 5-bromomethyl-5-(t-butyldiphenylsiloxymethyl)-2,2-dimethyl-1,3-dioxane was dissolved in 36 mL of dimethylformamide, 402 mg (3.56 mmol equivalents) of 2-nitroimidazole and 1.48 g (10.7 mmol equivalents) of potassium carbonate were added thereto, and the mixture was heated in an oil bath to 80° C. and then stirred for 18 hours. After completion of the reaction, water was added dropwise, and the mixture was extracted with ethyl acetate three times. The combined ethyl acetate layers were washed with water and brine, then dried with anhydrous magnesium sulfate, and subsequently concentrated under vacuum. The obtained crude product was purified by silica gel column chromatography (eluent: hexane/ethyl acetate (v/v)=3/1) to give 362 mg (0.71 mmol equivalents) of 5-(t-butyldiphenylsiloxymethyl)-2,2-dimethyl-5-[(2-nitro-1H-imidazol-1-yl)methyl]-1,3-dioxane.

$^1$H-NMR (solvent: deuterated chloroform) of 5-(t-butyldiphenylsiloxymethyl)-2,2-dimethyl-5-[(2-nitro-1H-imidazol-1-yl)methyl]-1,3-dioxane: δ 7.61-7.56 (m, 4H), 7.40-7.35 (m, 6H), 7.00 (s, 1H), 6.98 (s, 1H), 4.73 (s, 2H), 3.69 (d, J=12.4 Hz, 2H), 3.49 (d, J=12.4 Hz, 2H), 3.49 (s, 2H), 1.35 (s, 3H), 1.30 (s, 3H), 1.08 (s, 9H).

Synthesis of 5-{(4-bromo-2-nitro-1H-imidazol-1-yl)methyl}-5-(t-butyldiphenylsiloxymethyl)-2,2-dimethyl-1,3-dioxane (FIG. 4, Step 3)

315 mg (0.62 mmol equivalents) of 5-(t-butyldiphenylsiloxymethyl)-2,2-dimethyl-5-(2-nitro-1H-imidazol-1-yl)-1,3-dioxane was dissolved in 6 mL of dimethylformamide, 110 mg (0.62 mmol equivalents) of N-bromosuccinimide was added thereto, and the mixture was stirred at room temperature (25° C.) for 17 hours. After completion of the reaction, a saturated aqueous solution of sodium bicarbonate was added dropwise, subsequently a saturated aqueous solution of sodium thiosulfate was added dropwise, and the mixture was then extracted three times with ethyl acetate. The combined ethyl acetate layers were then dried with anhydrous magnesium sulfate and subsequently concentrated under vacuum, and the obtained crude product was purified by silica gel column chromatography (eluent: hexane/ethyl acetate (v/v)=4/1) to give 131 mg (0.22 mmol equivalents) of 5-{(4-bromo-2-nitro-1H-imidazol-1-yl)methyl}-5-(t-butyldiphenylsiloxymethyl)-2,2-dimethyl-1,3-dioxane.

¹H-NMR (solvent: deuterated chloroform) of 5-{(4-bromo-2-nitro-1H-imidazol-1-yl)methyl}-5-(t-butyldiphenylsiloxymethyl)-2,2-dimethyl-1,3-dioxane: δ 7.60-7.56 (m, 4H), 7.49-7.45 (m, 2H), 7.43-7.40 (m, 4H), 6.99 (s, 1H), 4.76 (s, 2H), 3.68 (d, J=12.4 Hz, 2H), 3.48 (d, J=12.4 Hz, 2H), 3.47 (s, 2H), 1.37 (s, 3H), 1.31 (s, 3H), 1.08 (s, 9H).

The reactions of Step 1 to Step 3 shown in FIG. 4 were repeated to thus synthesize an amount of 5-{(4-bromo-2-nitro-1H-imidazol-1-yl)methyl}-5-(t-butyldiphenylsiloxymethyl)-2,2-dimethyl-1,3-dioxane sufficient to be used in the following step.

Synthesis of 5-(t-butyldiphenylsiloxymethyl)-2,2-dimethyl-5-[(4-vinyl-2-nitro-1H-imidazol-1-yl)methyl]-1,3-dioxane (FIG. 4, Step 4)

280 mg (0.48 mmol equivalents) of 5-{(4-bromo-2-nitro-1H-imidazol-1-yl)methyl}-5-(t-butyldiphenylsiloxymethyl)-2,2-dimethyl-1,3-dioxane was dissolved in 4.7 mL of dimethylformamide, 278 μL (0.95 mmol equivalents) of tributylvinyltin and 55 mg (0.05 mmol equivalents) of tetrakis(triphenylphosphine)palladium were added thereto, and the mixture was heated to 80° C. in an oil bath and then stirred for 5 hours. After completion of the reaction, the reaction liquid was concentrated under vacuum, and the obtained crude product was purified by silica gel column chromatography (eluent: hexane/ethyl acetate (v/v)=4/1) to give 163 mg (0.30 mmol equivalents) of 5-(t-butyldiphenylsiloxymethyl)-2,2-dimethyl-5-[(4-vinyl-2-nitro-1H-imidazol-1-yl)methyl]-1,3-dioxane.

1H-NMR (solvent: deuterated chloroform) of 5-(t-butyldiphenylsiloxymethyl)-2,2-dimethyl-5-[(4-vinyl-2-nitro-1H-imidazol-1-yl)methyl]-1,3-dioxane: δ 7.60-7.58 (m, 4H), 7.47-7.44 (m, 2H), 7.42-7.38 (m, 4H), 6.96 (s, 1H), 6.43 (dd, J=11.0, 17.4 Hz, 1H), 5.88 (d, J=17.4 Hz, 1H), 5.30 (d, J=11.0 Hz, 1H), 4.71 (s, 2H), 3.69 (d, J=12.4 Hz, 2H), 3.53 (d, J=12.4 Hz, 2H), 3.52 (s, 2H), 1.39 (s, 3H), 1.31 (s, 3H), 1.09 (s, 9H).

Synthesis of 5-(t-butyldiphenylsiloxymethyl)-2,2-dimethyl-5-[(4-formyl-2-nitro-1H-imidazol-1-yl)methyl]-1,3-dioxane (FIG. 4, Step 5)

2.0 mL of a mixed solution of water/1,4-dioxane=3/1 was added to 163 mg (0.30 mmol equivalents) of 5-(t-butyldiphenylsiloxymethyl)-2,2-dimethyl-5-[(4-vinyl-2-nitro-1H-imidazol-1-yl)methyl]-1,3-dioxane, 38 mg (microcapsules, Wako Pure Chemical Industries, Ltd., 0.015 mmol equivalents) of osmium oxide and 130 mg (0.60 mmol equivalents) of sodium iodate were added thereto, and the mixture was stirred at room temperature (25° C.) for 5 days. After completion of the reaction, the osmium oxide was taken out, and the reaction liquid was extracted three times with ethyl acetate. The combined ethyl acetate layers were washed with water and brine, then dried with anhydrous magnesium sulfate, and subsequently concentrated under vacuum. The obtained crude product was purified by silica gel column chromatography (eluent: hexane/ethyl acetate (v/v)=5/1) to give 107 mg (0.20 mmol equivalents) of 5-(t-butyldiphenylsiloxymethyl)-2,2-dimethyl-5-[(4-formyl-2-nitro-1H-imidazol-1-yl)methyl]-1,3-dioxane.

¹H-NMR (solvent: deuterated chloroform) of 5-(t-butyldiphenylsiloxymethyl)-2,2-dimethyl-5-[(4-formyl-2-nitro-1H-imidazol-1-yl)methyl]-1,3-dioxane: δ 9.86 (s, 1H), 7.67 (s, 1H), 7.59-7.57 (m, 4H), 7.48-7.40 (m, 6H), 4.86 (s, 2H), 3.66 (d, J=12.6 Hz, 2H), 3.57 (d, J=12.6 Hz, 2H), 3.42 (s, 2H), 1.31 (s, 3H), 1.29 (s, 3H), 1.07 (s, 9H).

Synthesis of 5-(t-butyldiphenylsiloxymethyl)-2,2-dimethyl-5-{(4-hydroxymethyl-2-nitro-1H-imidazol-1-yl)methyl}-1,3-dioxane (FIG. 4, Step 6)

107 mg (0.20 mmol equivalents) of 5-(t-butyldiphenylsiloxymethyl)-2,2-dimethyl-5-[(4-formyl-2-nitro-1H-imidazol-1-yl)methyl]-1,3-dioxane was dissolved in 3.0 mL of ethanol, 10 mg (0.24 mmol equivalents) of sodium borohydride was added thereto, and the mixture was stirred at room temperature (25° C.) for 10 minutes. After completion of the reaction, acetone was added dropwise, and the mixture was concentrated under vacuum. The obtained crude product was purified by silica gel column chromatography (eluent: hexane/ethyl acetate (v/v)=1/1) to give 101 mg (0.19 mmol equivalents) of 5-(t-butyldiphenylsiloxymethyl)-2,2-dimethyl-5-{(4-hydroxymethyl-2-nitro-1H-imidazol-1-yl)methyl}-1,3-dioxane.

¹H-NMR (solvent: deuterated chloroform) of 5-(t-butyldiphenylsiloxymethyl)-2,2-dimethyl-5-{(4-hydroxymethyl-2-nitro-1H-imidazol-1-yl)methyl}-1,3-dioxane: δ 7.61-7.59 (m, 4H), 7.48-7.45 (m, 2H), 7.43-7.39 (m, 4H), 6.96 (s, 1H), 4.72 (s, 2H), 4.51 (d, J=6.5 Hz, 2H), 3.69 (d, J=12.4 Hz, 2H), 3.53 (d, J=12.4 Hz, 2H), 3.52 (s, 2H), 1.90 (t, J=6.5 Hz, 1H), 1.38 (s, 3H), 1.32 (s, 3H), 1.09 (s, 9H).

Synthesis of 5-(t-butyldiphenylsiloxymethyl)-2,2-dimethyl-5-[(4-methoxymethoxymethyl-2-nitro-1H-imidazol-1-yl)methyl]-1,3-dioxane (FIG. 4, Step 7)

101 mg (0.19 mmol equivalents) of 5-(t-butyldiphenylsiloxymethyl)-2,2-dimethyl-5-[(4-hydroxymethyl-2-nitro-1H-imidazol-1-yl)methyl]-1,3-dioxane was dissolved in 2.0 mL of dichloromethane and cooled to about 0° C. in an ice bath. 125 μL (0.72 mmol equivalents) of N,N-diisopropylethylamine and 41 μL (0.51 mmol equivalents) of methoxymethyl chloride were added thereto, and the mixture was stirred for 26 hours while increasing the temperature to room temperature (25° C.). After completion of the reaction, a saturated aqueous solution of sodium bicarbonate was added dropwise, and the mixture was extracted three times with ethyl acetate. The combined ethyl acetate layers were washed with water and brine, then dried with anhydrous magnesium sulfate, and subsequently concentrated under vacuum. The obtained crude product was purified by silica gel column chromatography (eluent: hexane/ethyl acetate (v/v)=2/1) to give 86 mg (0.15 mmol equivalents) of 5-(t-butyldiphenylsiloxymethyl)-2,2-dimethyl-5-[(4-methoxymethoxymethyl-2-nitro-1H-imidazol-1-yl)methyl]-1,3-dioxane.

¹H-NMR (solvent: deuterated chloroform) of 5-(t-butyldiphenylsiloxymethyl)-2,2-dimethyl-5-[(4-methoxymethoxymethyl-2-nitro-1H-imidazol-1-yl)methyl]-1,3-dioxane: δ 7.64-7.58 (m, 4H), 7.48-7.45 (m, 2H), 7.43-7.39 (m, 4H), 7.06 (s, 1H), 4.74 (s, 2H), 4.69 (s, 2H), 4.47 (s, 2H), 3.70 (d, J=12.4 Hz, 2H), 3.52 (d, J=12.4 Hz, 2H), 3.51 (s, 2H), 3.37 (s, 3H), 1.37 (s, 3H), 1.31 (s, 3H), 1.07 (s, 9H).

Synthesis of 2,2-dimethyl-5-hydroxymethyl-5-{(4-methoxymethoxymethyl-2-nitro-1H-imidazol-1-yl)methyl}-1,3-dioxane (FIG. 4, Step 8 1))

86 mg (0.15 mmol equivalents) of 5-(t-butyldiphenylsiloxymethyl)-2,2-dimethyl-5-[(4-methoxymethoxymethyl-2-nitro-1H-imidazol-1-yl)methyl]-1,3-dioxane was dissolved in 1.0 mL of tetrahydrofuran, 0.17 mL (1 mol/L solution, 0.17 mmol equivalents) of a solution of tetrabutylammonium fluoride in tetrahydrofuran was added thereto, and the mixture was stirred at room temperature (25° C.) for 10 minutes. After completion of the reaction, the solvent was removed by distillation, and the obtained crude product was purified by silica gel column chromatography (eluent: hexane/ethyl acetate (v/v)=1/1) to give 47 mg (0.14 mmol equivalents) of 2,2-dimethyl-5-hydroxymethyl-5-{(4-methoxymethoxymethyl-2-nitro-1H-imidazol-1-yl)methyl}-1,3-dioxane.

$^1$H-NMR (solvent: deuterated chloroform) of 2,2-dimethyl-5-hydroxymethyl-5-{(4-methoxymethoxymethyl-2-nitro-1H-imidazol-1-yl)methyl}-1,3-dioxane: δ 7.30 (s, 1H), 4.80 (s, 2H), 4.72 (s, 2H), 4.57 (s, 2H), 3.78 (d, J=12.4 Hz, 2H), 3.60 (d, J=12.4 Hz, 2H), 3.49 (s, 2H), 3.41 (s, 3H), 1.47 (s, 3H), 1.45 (s, 3H).

Synthesis of 2,2-dimethyl-5-[(4-methoxymethoxymethyl-2-nitro-1H-imidazol-1-yl)methyl]-5-(p-toluenesulfonyloxymethyl)-1,3-dioxane (FIG. 4, Step 8 2))

23 mg (0.11 mmol equivalents) of 2,2-dimethyl-5-hydroxymethyl-5-[(4-methoxymethoxymethyl-2-nitro-1H-imidazol-1-yl)methyl]-1,3-dioxane was dissolved in 1.0 mL of triethylamine, 1 mg (0.01 mmol equivalents) of N,N-dimethylaminopyridine and 23 mg (0.12 mmol equivalents) of p-toluenesulfonyl chloride were added thereto, and the mixture was stirred at room temperature (25° C.) for 16 hours. After completion of the reaction, a saturated aqueous solution of ammonium chloride was added, and the mixture was extracted three times with ethyl acetate. The combined ethyl acetate layers were dried with anhydrous magnesium sulfate, and then concentrated under vacuum. The obtained crude product was purified by flash silica gel column chromatography (eluent: hexane/ethyl acetate (v/v)=1/3) to give 16 mg (0.03 mmol equivalents) of 2,2-dimethyl-5-[(4-methoxymethoxymethyl-2-nitro-1H-imidazol-1-yl)methyl]-5-(p-toluenesulfonyloxymethyl)-1,3-dioxane.

$^1$H-NMR (solvent: deuterated dimethylsulfoxide) of 2,2-dimethyl-5-[(4-methoxymethoxymethyl-2-nitro-1H-imidazol-1-yl)methyl]-5-(p-toluenesulfonyloxymethyl)-1,3-dioxane: δ 7.75 (d, J=8.3 Hz, 2H), 7.38 (d, J=8.3 Hz, 2H), 7.20 (s, 1H), 4.73-4.71 (m, 4H), 4.55 (s, 2H), 3.93 (s, 2H), 3.74 (d, J=12.4 Hz, 2H), 3.60 (d, J=12.4 Hz, 2H), 3.41 (s, 3H), 2.47 (s, 3H), 1.40 (s, 3H), 1.35 (s, 3H).

Example 5

Figure 5:
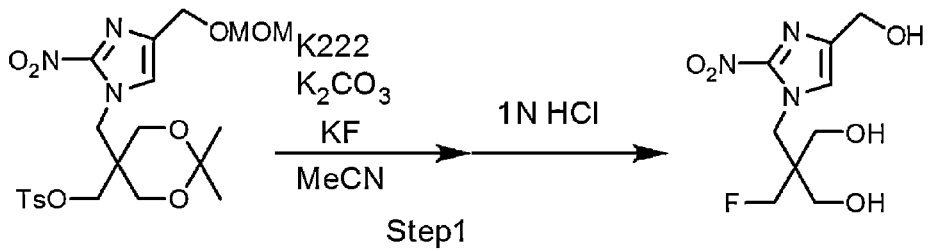
FIG. 5 is a synthetic scheme for 1-(2,2-dihydroxymethyl-3-fluoropropyl)-4-hydroxymethyl-2-nitroimidazole.

Production of 1-(2,2-dihydroxymethyl-3-fluoropropyl)-4-hydroxymethyl-2-nitroimidazole 1-(2,2-Dihydroxymethyl-3-fluoropropyl)-4-hydroxymethyl-2-nitroimidazole is a compound (non-radioactive compound 2) having the same structure as that of compound 2 except that the fluorine atom of compound 2 is changed from fluorine 18 to fluorine 19. FIG. 5 shows the synthetic scheme therefor.

3.6 mg (7.6 μmol equivalents) of 2,2-dimethyl-5-[(4-methoxymethoxymethyl-2-nitro-1H-imidazol-1-yl)methyl]-5-(p-toluenesulfonyloxymethyl)-1,3-dioxane was dissolved in 1 mL of acetonitrile, 17 mg (34.5 μmol equivalents) of Kryptofix 222 (trade name, Merck), 5.8 mg (100 μmol equivalents) of potassium fluoride, and 1.8 mg (23 μmol equivalents) of potassium carbonate were added thereto, and the mixture was refluxed while heating for 3 hours. After completion of the reaction, water was added, and the mixture was extracted three times with chloroform. The combined chloroform layers were dried with anhydrous sodium sulfate and then concentrated under vacuum. The obtained crude product was purified by silica gel column chromatography (eluent: hexane/ethyl acetate (v/v)=1/1). 1 mL of 1 mol/L hydrochloric acid was added dropwise to a fraction thus obtained, and the mixture was heated to 80° C. in an oil bath and then stirred for 50 minutes. After completion of the reaction, the mixture was concentrated under vacuum to give a trace amount of 1-(2,2-dihydroxymethyl-3-fluoropropyl)-4-hydroxymethyl-2-nitroimidazole.

$^1$H-NMR (solvent: deuterated chloroform) of 1-(2,2-dihydroxymethyl-3-fluoropropyl)-4-hydroxymethyl-2-nitroimidazole: δ 6.99 (s, 1H), 4.77-4.76 (m, 4H), 4.57-4.55 (m, 2H), 4.48-4.46 (m, 2H), 3.63-3.60 (m, 2H).

$^{19}$F-NMR (solvent: deuterated chloroform) of 1-(2,2-dihydroxymethyl-3-fluoropropyl)-4-hydroxymethyl-2-nitroimidazole: δ −235.8 (t, $J_{H-F}$=46.7 Hz, 1F).

Example 6

Production of 1-(2,2-dihydroxymethyl-3-[$^{18}$F]fluoropropyl)-4-hydroxymethyl-2-nitroimidazole (Compound 2)

Figure 6:
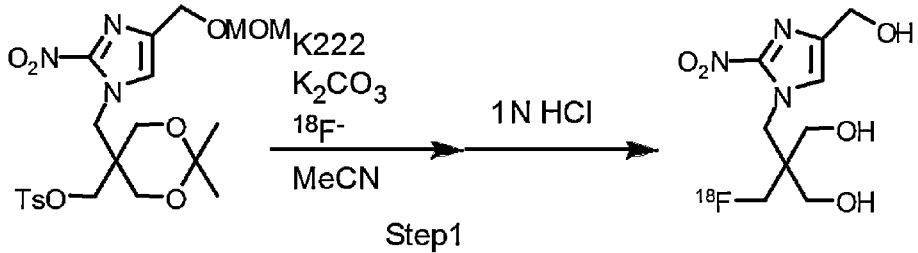
FIG. 6 is a synthetic scheme for 1-(2,2-dihydroxymethyl-3-[$^{18}$F]fluoropropyl)-4-hydroxymethyl-2-nitroimidazole.

FIG. 6 shows the synthetic scheme therefor.

[$^{18}$F]Fluoride ion-containing $H_2{}^{18}O$ (amount of radioactivity 2.37 GBq, value corrected when synthesis started) was passed through an anion-exchange column (Sep-Pak (registered trademark) Accell Plus QMA Plus Light (trade name), manufactured by Nihon Waters K.K.) that had been pretreated with an aqueous solution of potassium carbonate to collect [$^{18}$F]fluoride ion by adsorption. Subsequently, an aqueous solution of potassium carbonate (42.4 μmol/L, 0.3 mL) and a solution of 14 mg (37.2 μmol equivalents) of Kryptofix 222 (trade name, Merck) in 0.7 mL of acetonitrile were passed through this column to thus elute [$^{18}$F]fluoride ion.

This eluate was heated under a flow of argon gas to 110° C. so as to evaporate water, acetonitrile (0.3 mL×2) was then added, and the mixture was subjected to azeotropic distillation to dryness. 0.3 mL of a solution of 5 mg (10 μmol equivalents) of 2,2-dimethyl-5-[(4-methoxymethoxymethyl-2-nitro-1H-imidazol-1-yl)methyl]-5-(p-toluenesulfonyloxymethyl)-1,3-dioxane synthesized in the Example 4 dissolved in acetonitrile was added thereto, and the mixture was heated at 110° C. for 10 minutes. Subsequently, 0.3 mL of 1 mol/L hydrochloric acid was added, and the mixture was heated at 110° C. for 3 minutes. After completion of the reaction, the mixture was cooled to room temperature, 1.0 mL of water for injection was added, and the mixture was subjected to HPLC (mobile phase: 0.1% (v/v) trifluoroacetic acid aqueous solution/acetonitrile (containing 0.1% (v/v) trifluoroacetic acid) (v/v)=90/10, flow rate: 3.0 mL/min) and identified using the non-radioactive compound 2 obtained in the Example 5 such that a peak at a retention time of 13 minutes was a fraction of compound 2, and the fraction of compound 2 thus identified was collected.

10 mL of water was added to this fraction, and the liquid thus obtained was passed through a Sep-Pak (registered trademark) HLB Plas (trade name, manufactured by Nihon Waters K.K.) to collect compound 2 on this column by absorption. This column was washed with 3 mL of water, and 2 mL of ethanol was then passed through to thus elute compound 2. The obtained amount of radioactivity was 143 MBq (87 minutes after start of synthesis). When TLC analysis of compound 2 was carried out, it was found that the radiochemical purity was 98%.

Example 7

Figure 7:
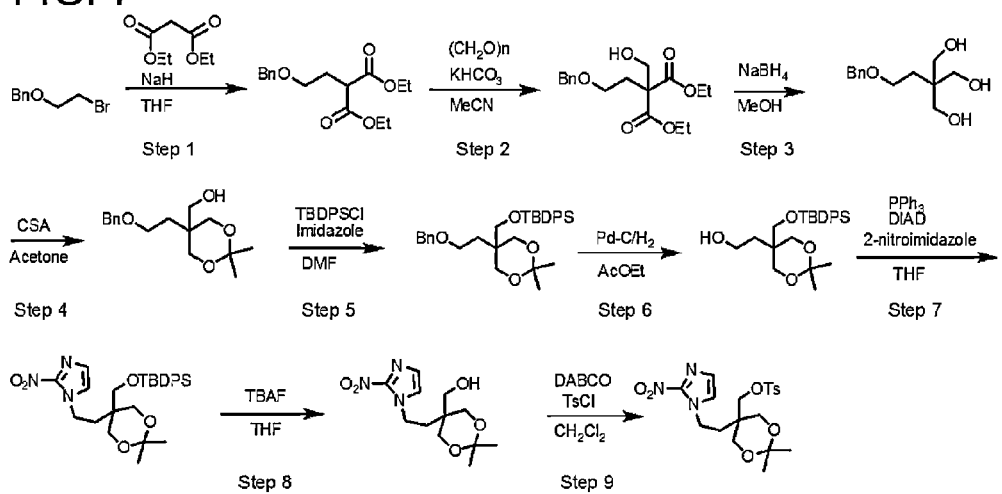
FIG. 7A diagram showing a synthetic scheme for 2,2-dimethyl-5-[2-(2-nitro-1H-imidazol-1-yl)ethyl]-5-(p-toluenesulfonyloxymethyl)-1,3-dioxane.

Synthesis of 2,2-dimethyl-5-[2-(2-nitro-1H-imidazol-1-yl)ethyl]-5-(p-toluenesulfonyloxymethyl)-1,3-dioxane 2,2-Dimethyl-5-[2-(2-nitro-1H-imidazol-1-yl)ethyl]-5-(p-toluenesulfonyloxymethyl)-1,3-dioxane is a labeling precursor of compound 3. FIG. 7 shows the synthetic scheme therefor.

Synthesis of diethyl 2-(2-benzyloxyethyl)malonate (FIG. 7, Step 1)

506 mg (60% in oil, 13 mmol equivalents) of sodium hydride was added to 5.0 mL of tetrahydrofuran, and the mixture was cooled to about 0° C. in an ice bath. 3.2 mL (20.7 mmol equivalents) of diethyl malonate was added thereto (solution A). 2.3 g (10.7 mmol equivalents) of 2-benzyloxy-1-bromoethane was dissolved in 3.0 mL of tetrahydrofuran, this was added dropwise to solution A over 10 minutes, and the mixture was refluxed while heating overnight. After completion of the reaction, a 0.5 mol/L aqueous solution of hydrochloric acid was added dropwise to the reaction liquid, and the mixture was extracted three times with diethyl ether. The combined diethyl ether layers were washed with brine, then dried with anhydrous magnesium sulfate, and subsequently concentrated under vacuum, and the obtained crude product was purified by silica gel column chromatography (eluent: hexane/ethyl acetate (v/v)=20/1) to give 2.85 g (9.67 mmol equivalents) of diethyl 2-(2-benzyloxyethyl)malonate.

$^1$H-NMR (solvent: deuterated chloroform) of diethyl 2-(2-benzyloxyethyl)malonate: δ 7.36-7.28 (m, 5H), 4.48 (s, 2H), 4.21-4.14 (m, 4H), 3.60 (d, J=7.3 Hz, 1H), 3.53 (t, J=5.5 Hz, 2H), 2.22 (dt, J=5.5, 7.3 Hz, 2H), 1.25 (t, J=7.3 Hz, 6H).

Synthesis of diethyl 2-(2-benzyloxyethyl)-2-hydroxymethylmalonate (FIG. 7, Step 2)

2.85 g (9.67 mmol equivalents) of diethyl 2-(2-benzyloxyethyl)malonate was dissolved in 20 mL of acetonitrile, 1.60 g (11.7 mmol equivalents) of potassium bicarbonate and 465 mg (11.7 mmol equivalents as formaldehyde) of paraformaldehyde were added thereto, and the mixture was stirred at room temperature (25° C.) overnight. After completion of the reaction, a 0.5 mol/L aqueous solution of hydrochloric acid was added dropwise to the reaction liquid, and the mixture was extracted three times with chloroform. The combined chloroform layers were dried with anhydrous magnesium sulfate and then concentrated under vacuum, and the obtained crude product was purified by silica gel column chromatography (eluent: hexane/ethyl acetate (v/v)=4/1) to give 2.78 g (8.76 mmol equivalents) of diethyl 2-(2-benzyloxyethyl)-2-hydroxymethylmalonate.

$^1$H-NMR (solvent: deuterated chloroform) of diethyl 2-(2-benzyloxyethyl)-2-hydroxymethylmalonate: δ 7.36-7.27 (m, 5H), 4.48 (s, 2H), 4.18 (m, 4H), 4.03 (d, J=7.3 Hz, 2H), 3.60 (t, J=5.5 Hz, 2H), 3.03 (t, J=7.3 Hz, 1H), 2.33 (t, J=5.5 Hz, 2H), 1.24 (t, J=7.3 Hz, 6H).

Synthesis of 4-benzyloxy-2,2-dihydroxymethylbutanol (FIG. 7, Step 3)

1.03 g (3.24 mmol equivalents) of diethyl 2-(2-benzyloxyethyl)-2-hydroxymethylmalonate was dissolved in 10 mL of methanol, and this was added dropwise to 1.69 g (44.6 mmol equivalents) of sodium borohydride over 20 minutes. This was refluxed while heating overnight and then cooled to room temperature (25° C.). Water was added to the reaction liquid, and a reaction was carried out for 30 minutes. The reaction liquid was washed with chloroform, and the aqueous phase was concentrated under vacuum. 100 mL of ethanol was added to the obtained residue, and the mixture was refluxed while heating for 2 hours. Immediately after completion of the reaction, the mixture was subjected to silica gel column chromatography (eluent: ethanol) to give 543 mg of 4-benzyloxy-2,2-dihydroxymethylbutanol as an crude product.

$^1$H-NMR (solvent: deuterated chloroform) of 4-benzyloxy-2,2-dihydroxymethylbutanol: δ 7.36-7.29 (m, 5H), 4.50 (s, 2H), 3.87 (brs, 2H), 3.71-3.65 (m, 2H), 3.59-3.53 (m, 7H), 1.21 (m, 2H).

Synthesis of 5-benzyloxyethyl-2,2-dimethyl-5-hydroxymethyl-1,3-dioxane (FIG. 7, Step 4)

543 mg of the crude 4-benzyloxy-2,2-dihydroxymethylbutanol product was dissolved in 3 mL of acetone, 232 mg (1.0 mmol equivalents) of 10-camphorsulfonic acid was added thereto, and a reaction was carried out at room temperature (25° C.) overnight. After completion of the reaction, triethylamine was added dropwise, and the mixture was concentrated under vacuum. The crude product thus obtained was purified by silica gel column chromatography (eluent: hexane/ethyl acetate (v/v)=4/1) to give 459 mg (1.64 mmol equivalents) of 5-benzyloxyethyl-2,2-dimethyl-5-hydroxymethyl-1,3-dioxane.

$^1$H-NMR (solvent: deuterated chloroform) of 5-benzyloxyethyl-2,2-dimethyl-5-hydroxymethyl-1,3-dioxane: δ 7.37-7.28 (m, 5H), 4.52 (s, 2H), 3.70 (d, J=11.9 Hz, 2H), 3.61-3.57 (m, 6H), 3.15 (t, J=6.9 Hz, 1H), 1.74 (t, J=5.5 Hz, 2H), 1.40 (s, 6H).

Synthesis of 5-benzyloxyethyl-2,2-dimethyl-5-(t-butyldiphenylsiloxymethyl)-1,3-dioxane (FIG. 7, Step 5)

459 mg (1.64 mmol equivalents) of 5-benzyloxyethyl-2,2-dimethyl-5-hydroxymethyl-1,3-dioxane was dissolved in 8 mL of dimethylformamide, 197 mg (3.20 mmol equivalents) of imidazole and 0.51 mL (1.92 mmol equivalents) of t-butyldiphenylchlorosilane were added thereto, and the mixture was stirred at room temperature (25° C.) for 22 hours. After completion of the reaction, a saturated aqueous solution of ammonium chloride was added thereto, and the mixture was extracted three times with ethyl acetate. The combined ethyl acetate layers were washed with water and brine, then dried with anhydrous magnesium sulfate, and subsequently concentrated under vacuum. The obtained crude product was purified by silica gel column chromatography (eluent: hexane/ethyl acetate (v/v)=20/1) to give 570 mg (1.56 mmol equivalents) of 5-benzyloxyethyl-2,2-dimethyl-5-(t-butyldiphenylsiloxymethyl)-1,3-dioxane.

$^1$H-NMR (solvent: deuterated chloroform) of 5-benzyloxyethyl-2,2-dimethyl-5-(t-butyldiphenylsiloxymethyl)-1,3-dioxane: δ 7.68-7.66 (m, 4H), 7.43-7.35 (m, 7H), 7.33-7.25 (m, 4H), 4.39 (s, 2H), 3.79 (d, J=12.4 Hz, 2H), 3.76 (s, 2H), 3.69 (d, J=12.4 Hz, 2H), 3.51 (t, J 10=6.4 Hz, 2H), 1.66 (t, J=6.4 Hz, 2H), 1.41 (s, 3H), 1.33 (s, 3H), 1.05 (s, 9H).

Synthesis of 5-(t-butyldiphenylsiloxymethyl)-2,2-dimethyl-5-hydroxyethyl-1,3-dioxane (FIG. 7, Step 6)

570 mg (1.56 mmol equivalents) of 5-benzyloxyethyl-2,2-dimethyl-5-(t-butyldiphenylsiloxymethyl)-1,3-dioxane was dissolved in 30 mL of ethyl acetate, 100 mg of palladium carbon was added thereto under argon atmosphere, and the mixture was stirred under hydrogen atmosphere at room temperature (25° C.) for 22 hours. After completion of the reaction, a precipitate was filtered, and the filtrate was concentrated under vacuum. The obtained crude product was purified by silica gel column chromatography (eluent: hexane/ethyl acetate (v/v)=4/1) to give 174 mg (0.41 mmol equivalents) of 5-(t-butyldiphenylsiloxymethyl)-2,2-dimethyl-5-hydroxyethyl-1,3-dioxane.

$^1$H-NMR (solvent: deuterated chloroform) of 5-(t-butyldiphenylsiloxymethyl)-2,2-dimethyl-5-hydroxyethyl-1,3-dioxane: δ 7.68-7.66 (m, 4H), 7.46-7.38 (m, 6H), 3.85 (d, J=12.4 Hz, 2H), 3.76 (dd, J=6.0, 6.0 Hz, 2H), 3.64 (d, J=12.4 Hz, 2H), 3.62 (s, 2H), 2.89 (t, J=6.0 Hz, 1H), 1.61 (t, J=6.0 Hz, 2H), 1.41 (s, 3H), 1.34 (s, 3H), 1.08 (s, 9H).

Synthesis of 5-(t-butyldiphenylsiloxymethyl)-2,2-dimethyl-5-[2-(2-nitro-1H-imidazol-1-yl)ethyl]-1,3-dioxane (FIG. 7, Step 7)

48 mg (0.112 mmol equivalents) of 5-(t-butyldiphenylsiloxymethyl)-2,2-dimethyl-5-hydroxyethyl-1,3-dioxane was dissolved in 1 mL of tetrahydrofuran, 32 mg (0.123 mmol equivalents) of triphenylphosphine, 24 μL (0.123 mmol equivalents) of diisopropyl azodicarboxylate, and 38 mg (0.336 mmol equivalents) of 2-nitroimidazole were added thereto, and the mixture was stirred at room temperature (25° C.) for 4 hours. After completion of the reaction, the mixture was concentrated under vacuum, and the obtained crude product was purified by silica gel column chromatography (eluent: hexane/ethyl acetate (v/v)=4/1) to give 46 mg (0.088 mmol equivalents) of 5-(t-butyldiphenylsiloxymethyl)-2,2-dimethyl-5-[2-(2-nitro-1H-imidazol-1-yl)ethyl]-1,3-dioxane.

$^1$H-NMR (solvent: deuterated chloroform) of 5-(t-butyldiphenylsiloxymethyl)-2,2-dimethyl-5-[2-(2-nitro-1H-imidazol-1-yl)ethyl]-1,3-dioxane: δ 7.68-7.66 (m, 4H), 7.46-7.38 (m, 6H), 7.11-7.13 (m, 1H), 6.96 (d, J=0.9 Hz, 1H), 4.51-4.47 (m, 2H), 3.83 (d, J=11.9 Hz, 2H), 3.69 (s, 2H), 3.69 (d, J=11.9 Hz, 2H), 1.89-1.86 (m, 2H), 1.42 (s, 3H), 1.37 (s, 3H), 1.09 (s, 9H).

Synthesis of 2,2-dimethyl-5-hydroxymethyl-5-[2-(2-nitro-1H-imidazol-1-yl)ethyl]-1,3-dioxane (FIG. 7, Step 8)

46 mg (0.088 mmol equivalents) of 5-(t-butyldiphenylsiloxymethyl)-2,2-dimethyl-5-[2-(2-nitro-1H-imidazol-1-yl)ethyl]-1,3-dioxane was dissolved in 1 mL of tetrahydrofuran, 0.11 mL (1 mol/L solution, 0.11 mmol equivalents) of a solution of tetrabutylammonium fluoride in tetrahydrofuran was added thereto, and the mixture was stirred at room temperature (25° C.) for 1 hour. After completion of the reaction, the solvent was removed by distillation, and the obtained crude product was purified by silica gel column chromatography (eluent: chloroform/methanol (v/v)=10/1) to give 25 mg (0.086 mmol equivalents) of 2,2-dimethyl-5-hydroxymethyl-5-[2-(2-nitro-1H-imidazol-1-yl)ethyl]-1,3-dioxane.

$^1$H-NMR (solvent: deuterated chloroform) of 2,2-dimethyl-5-hydroxymethyl-5-[2-(2-nitro-1H-imidazol-1-yl)ethyl]-1,3-dioxane: δ 7.15-7.14 (m, 2H), 4.59-4.46 (m, 2H), 3.79 (d, J=11.9 Hz, 2H), 3.78 (s, 2H), 3.72 (d, J=11.9 Hz, 2H), 1.90-1.87 (m, 2H), 1.44 (s, 3H), 1.42 (s, 3H).

Synthesis of 2,2-dimethyl-5-[2-(2-nitro-1H-imidazol-1-yl)ethyl]-5-(p-toluenesulfonyloxymethyl)-1,3-dioxane (FIG. 7, Step 9)

25 mg (0.086 mmol equivalents) of 2,2-dimethyl-5-hydroxymethyl-5-[2-(2-nitro-1H-imidazol-1-yl)ethyl]-1,3-dioxane was dissolved in 1 mL of dichloromethane, 19 mg (0.172 mmol equivalents) of 1,4-diazabicyclo[2,2,2]octane and 19 mg (0.10 mmol equivalents) of p-toluenesulfonyl chloride were added thereto, and the mixture was stirred at room temperature (25° C.) for 4 hours. After completion of the reaction, a saturated aqueous solution of ammonium chloride was added, and the mixture was extracted three times with ethyl acetate. The combined ethyl acetate layers were dried with anhydrous magnesium sulfate and then concentrated under vacuum. The obtained crude product was purified by silica gel column chromatography (eluent: hexane/ethyl acetate (v/v)=1/3) to give 18 mg (0.041 mmol equivalents) of 2,2-dimethyl-5-[2-(2-nitro-1H-imidazol-1-yl)ethyl]-5-(p-toluenesulfonyloxymethyl)-1,3-dioxane.

$^1$H-NMR (solvent: deuterated chloroform) of 2,2-dimethyl-5-[2-(2-nitro-1H-imidazol-1-yl)ethyl]-5-(p-toluenesulfonyloxymethyl)-1,3-dioxane: δ 7.82 (d, J=8.3 Hz, 2H), 7.38 (d, J=8.3 Hz, 2H), 7.19 (s, 1H), 7.16 (s, 1H), 4.51-4.47 (m, 2H), 4.19 (s, 2H), 3.73 (d, J=11.9 Hz, 2H), 3.66 (d, J=11.9 Hz, 2H), 2.47 (s, 3H), 1.83-1.86 (m, 2H), 1.40 (s, 3H), 1.28 (s, 3H).

Example 8

Figure 8:
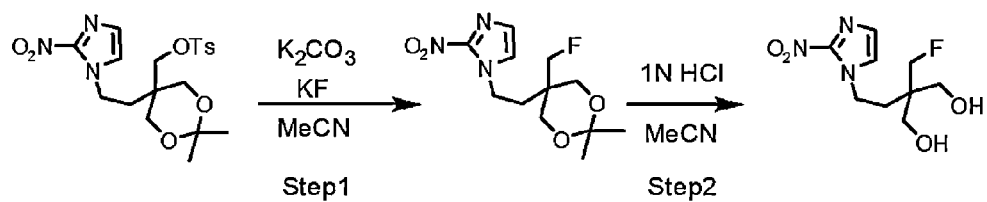
FIG. 8 is a synthetic scheme for 1-(3,3-dihydroxymethyl-4-fluorobutyl)-2-nitroimidazole.

Production of 1-(3,3-dihydroxymethyl-4-fluorobutyl)-2-nitroimidazole 1-(3,3-Dihydroxymethyl-4-fluorobutyl)-2-nitroimidazole is a compound (non-radioactive compound 3) having the same structure as that of compound 3 except that the fluorine atom of compound 3 is changed from fluorine 18 to fluorine 19. FIG. 8 shows the synthetic scheme therefor.

Synthesis of 2,2-dimethyl-5-fluoromethyl-5-[2-(2-nitro-1H-imidazol-1-yl)ethyl]-1,3-dioxane (FIG. 8, Step 1)

5 mg (11.4 μmol equivalents) of 2,2-dimethyl-5-[2-(2-nitro-1H-imidazol-1-yl)ethyl]-5-(p-toluenesulfonyloxymethyl)-1,3-dioxane was dissolved in 1 mL of acetonitrile, 14 mg (34.5 μmol equivalents) of Kryptofix 222 (trade name, Merck), 0.82 g (14.1 μmol equivalents) of potassium fluoride, and 0.4 mg (2.9 μmol equivalents) of potassium carbonate were added thereto, and the mixture was refluxed while heating for 5 hours. After completion of the reaction, water was added and the mixture was extracted three times with chloroform. The combined chloroform layers were dried with anhydrous magnesium sulfate and subsequently concentrated under vacuum. The obtained crude product was purified by silica gel column chromatography to give a trace amount of 2,2-dimethyl-5-fluoromethyl-5-[2-(2-nitro-1H-imidazol-1-yl)ethyl]-1,3-dioxane.

$^1$H-NMR (solvent: deuterated chloroform) of 2,2-dimethyl-5-fluoromethyl-5-[2-(2-nitro-1H-imidazol-1-yl) ethyl]-1,3-dioxane: δ 7.16 (s, 1H), 7.11 (s, 1H), 4.63-4.53 (m, 4H), 3.81-3.72 (m, 4H), 1.91-1.88 (m, 2H), 1.45 (s, 3H), 1.43 (s, 3H).

$^{19}$F-NMR (solvent: deuterated chloroform) of 2,2-dimethyl-5-fluoromethyl-5-[2-(2-nitro-1H-imidazol-1-yl)ethyl]-1,3-dioxane: δ −231.0 (t, $J_{H-F}$=49.0 Hz, 1F).

Synthesis of 1-(3,3-dihydroxymethyl-4-fluorobutyl)-2-nitroimidazole (FIG. 8, Step 2)

2,2-Dimethyl-5-fluoromethyl-5-[2-(2-nitro-1H-imidazol-1-yl)ethyl]-1,3-dioxane was dissolved in 0.5 mL of acetonitrile, 0.5 mL of 1 mol/L hydrochloric acid was added thereto, and the mixture was stirred at 80° C. for 30 minutes. After completion of the reaction, the mixture was concentrated under vacuum to give a trace amount of 1-(3,3-dihydroxymethyl-4-fluorobutyl)-2-nitroimidazole.

$^1$H-NMR (solvent: deuterated chloroform) of 1-(3,3-dihydroxymethyl-4-fluorobutyl)-2-nitroimidazole: δ 7.16 (s, 1H), 7.13 (s, 1H), 4.61-4.57 (m, 2H), 4.51 (d, $J_{H-F}$=47.2 Hz, 2H), 3.76-3.67 (m, 4H).

Example 9

Synthesis of 1-(3,3-dihydroxymethyl-4-[$^{18}$F]fluorobutyl)-2-nitroimidazole (Compound 3)

Figure 9:
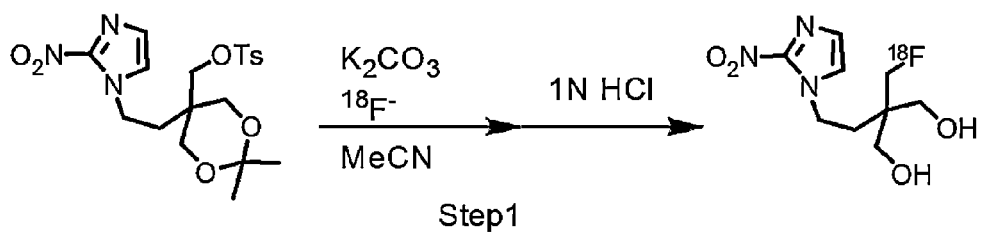
FIG. 9 is a synthetic scheme for 1-(3,3-dihydroxymethyl-4-[$^{18}$F]fluorobutyl)-2-nitroimidazole.

FIG. 9 shows the synthetic scheme therefor.

[$^{18}$F]Fluoride ion-containing $H_2^{18}O$ (amount of radioactivity 2.87 GBq, value corrected when synthesis started) was passed through an anion-exchange column (Sep-Pak (registered trademark) Accell Plus QMA Plus Light (trade name), manufactured by Nihon Waters K.K.) that had been pretreated with an aqueous solution of potassium carbonate to collect [$^{18}$F]fluoride ion by adsorption. Subsequently, an aqueous solution of potassium carbonate (42.4 μmol/L, 0.3 mL) and a solution of 14 mg (37.2 μmol equivalents) of Kryptofix 222 (trade name, Merck) in 0.7 mL of acetonitrile were passed through this column to thus elute [$^{18}$F]fluoride ion.

This eluate was heated under a flow of argon gas to 110° C. so as to evaporate water, acetonitrile (0.3 mL×2) was then added thereto, and the mixture was subjected to azeotropic distillation to dryness. 0.3 mL of a solution of 5 mg (11.4 μmol equivalents) of 2,2-dimethyl-5-[2-(2-nitro-1H-imidazol-1-yl)ethyl]-5-(p-toluenesulfonyloxymethyl)-1,3-dioxane synthesized in the Example 7 dissolved in acetonitrile was added thereto, and the mixture was heated at 110° C. for 10 minutes. Subsequently, 0.3 mL of 1 mol/L hydrochloric acid was added, and the mixture was heated at 110° C. for 3 minutes. After completion of the reaction, 1.0 mL of water was added, the mixture was subjected to HPLC (mobile phase: 0.1% (v/v) trifluoroacetic acid aqueous solution/acetonitrile (containing 0.1% (v/v) trifluoroacetic acid) (v/v)=85/15, flow rate: 2.5 mL/min), and identified using the non-radioactive of compound 3 obtained in the Example 8 such that a peak at a retention time of 16 minutes was a fraction of compound 3, and the fraction of compound 3 thus identified was collected.

10 mL of water was added to this fraction, the liquid thus obtained was passed through a Sep-Pak (registered trademark) HLB Plas (trade name, manufactured by Nihon Waters K.K.), and compound 3 was collected on the column by absorption. This column was washed with 3 mL of water, and 2 mL of ethanol was then passed through to thus elute compound 3. The obtained amount of radioactivity was 463 MBq (83 minutes after start of synthesis). When TLC analysis was carried out, it was found that the radiochemical purity was 99%.

Example 10

Incorporation into Tumor Cells

Accumulation of compound 1, compound 2, and compound 3 in tumor cells in vivo was studied as follows using a mouse-derived breast cancer cell line (EMT6).
(Method)
Preparation of tumor-bearing model mice: the animals used were six-week-old female Balb/c nu/nu mice (obtained from Japan SLC). Using these animals, a Matrigel suspension (cell count 2.5×10$^6$ cells/0.05 mL) of EMT6, which is a mouse-derived breast cancer cell line (obtained from ATCC), was subcutaneously implanted in a site from the right rib to the right shoulder. It was confirmed on the third day after implantation that the tumor cells were fixed, and the tumor volume attained 200 to 400 mm$^3$ 9 to 11 days after implantation.

Experimental method: compound 1, compound 2, compound 3, and [$^{18}$F]fluoromisonidazole ([$^{18}$F]FMISO) synthesized in accordance with a method of Rasey J S et al. (Int J Radiat Oncol Biol Phys, November; 17 (5): 985-991, 1989) were each diluted with 10 mg/mL ascorbic acid-containing physiological saline to give a sample solution having the radioactivity concentration adjusted to 1000 MBq/mL. The tumor-bearing model mouse thus prepared was placed under isoflurane anesthesia, and about 20 MBq of these sample solutions was administered via a tail vein. static imaging was carried out using a PET system for animals (model: eXplore Vista, manufactured by GE) at 60 minutes after administration. The collection time was 20 minutes for a tumor-bearing model mouse to which compound 1 had been administered, and 10 minutes for tumor-bearing model mice to which compound 2, compound 3 or [$^{18}$F]FMISO had been administered. Data thus collected were reconstituted by the OSEM method to thus form an image, and a coronal tomographic image and an axial tomographic image were formed using image analysis software.
(Results)

Figure 10:
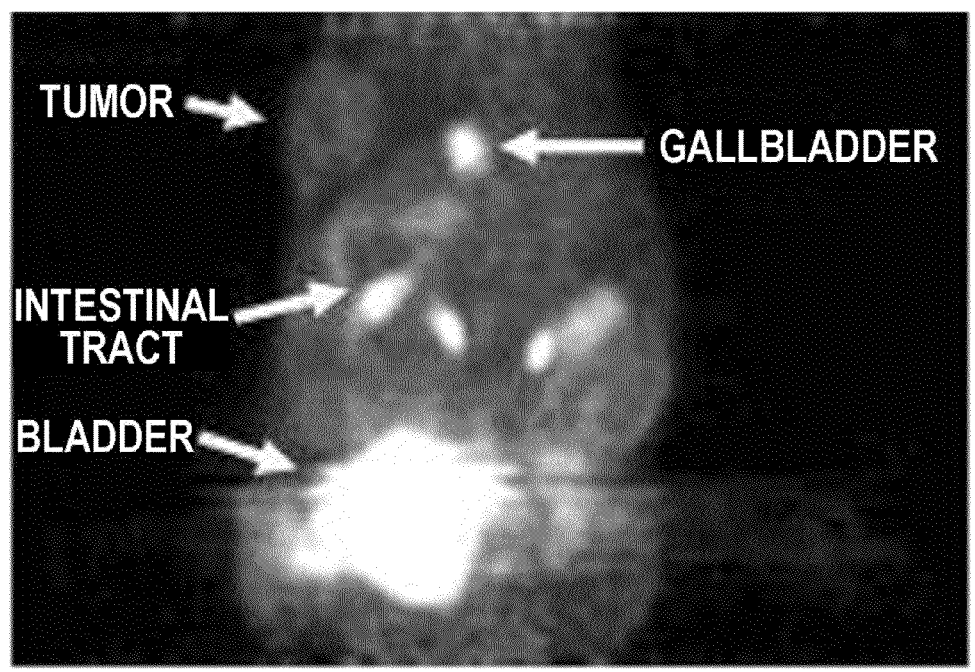
FIG. 10 is a coronal tomographic image of 1-(2,2-dihydroxymethyl-3-[$^{18}$F]fluoropropyl)-2-nitroimidazole in a tumor-bearing model mouse.
Figure 11:
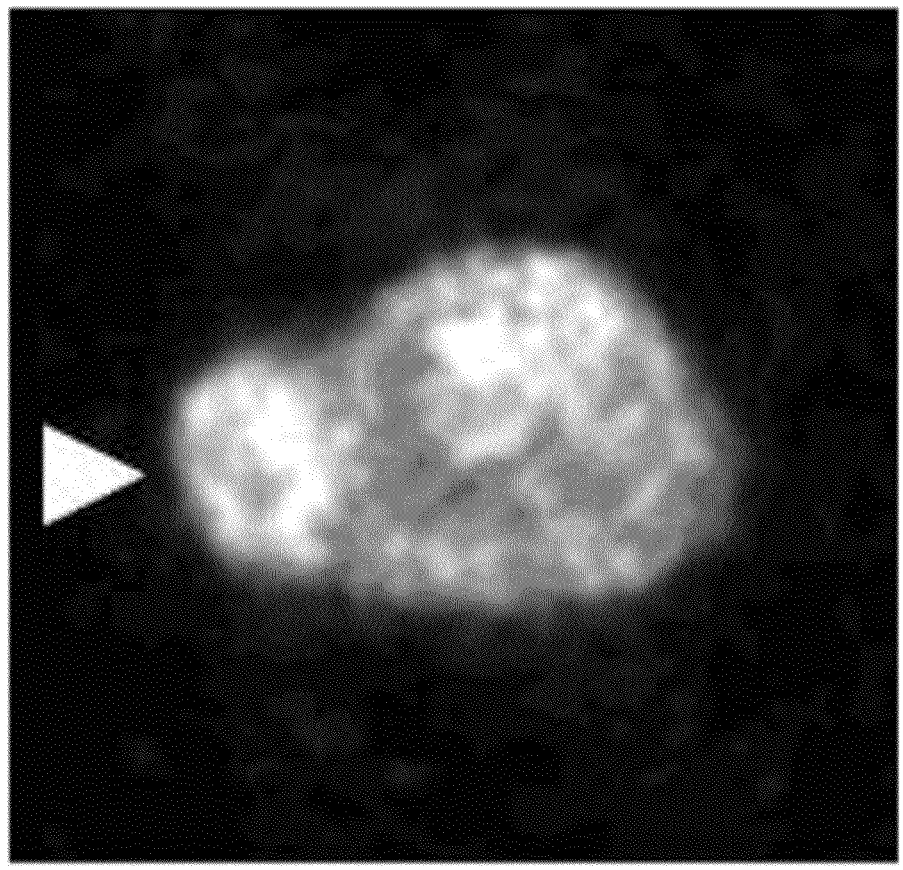
FIG. 11 is an axial tomographic image of 1-(2,2-dihydroxymethyl-3-[$^{18}$F]fluoropropyl)-2-nitroimidazole in a tumor-bearing model mouse.
Figure 12:
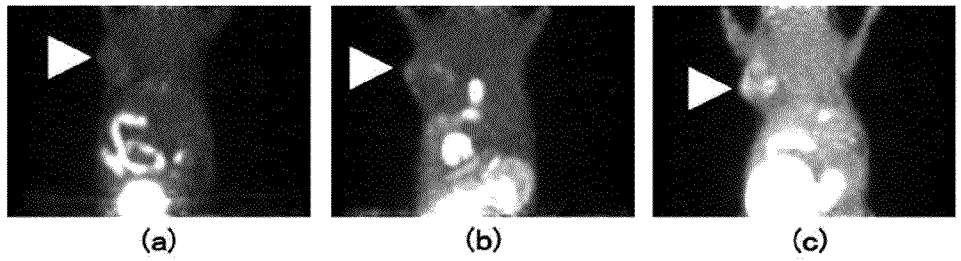
FIG. 12(a) is a coronal tomographic image of a tumor-bearing model mouse to which 1-(2,2-dihydroxymethyl-3-[$^{18}$F]fluoropropyl))-4-hydroxymethyl-2-nitroimidazole was administered.
FIG. 12(b) is a coronal tomographic image of a tumor-bearing model mouse to which 1-(3,3-dihydroxymethyl-4-[$^{18}$F]fluorobutyl)-2-nitroimidazole was administered.
FIG. 12(c) is a coronal tomographic image of a tumor-bearing model mouse to which [$^{18}$F]FMISO was administered.
Figure 13:
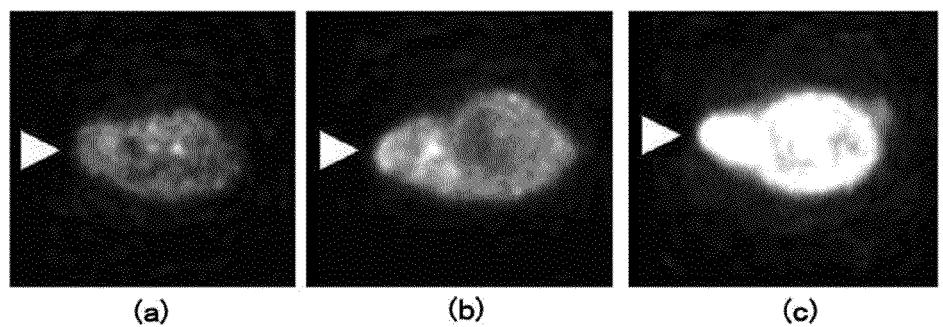
FIG. 13(a) is an axial tomographic image of a tumor-bearing model mouse to which 1-(2,2-dihydroxymethyl-3-[$^{18}$F]fluoropropyl)-4-hydroxymethyl-2-nitroimidazole was administered.
FIG. 13(b) is an axial tomographic image of a tumor-bearing model mouse to which 1-(3,3-dihydroxymethyl-4-[$^{18}$F]fluorobutyl)-2-nitroimidazole was administered.
FIG. 13(c) is an axial tomographic image of a tumor-bearing model mouse to which [$^{18}$F]FMISO was administered.

The results are shown in FIGS. 10 to 13. FIG. 10 is a coronal tomographic image of the tumor-bearing model mouse to which compound 1 had been administered. FIG. 11 is an axial tomographic image of the tumor-bearing model mouse to which compound 1 had been administered. FIG. 12(a), FIG. 12 (b), and FIG. 12 (c) are coronal tomographic images of tumor-bearing model mice. FIG. 12(a) is a image of a mouse to which compound 2 had been administered, FIG. 12(b) is a image of a mouse to which compound 3 had been administered, and FIG. 12(c) is a image of a mouse to which [$^{18}$F]FMISO had been administered. FIG. 13 (a), FIG. 13 (b), and FIG. 13 (c) are axial tomographic images of tumor-bearing model mice. FIG. 13 (a) is a image of a mouse to which compound 2 had been administered, FIG. 13 (b) is a image of a mouse to which compound 3 had been administered, and FIG. 13 (c) is a image of a mouse to which [$^{18}$F] FMISO had been administered. In FIGS. 11 to 13, the tumor sites are present in the direction of the extremities of the arrows.

From the coronal tomographic image (FIG. 10), it was found intense accumulation of compound 1 in the bladder, and accumulation thereof in the gallbladder and the intestinal tract at 60 minutes after administration. These results show that it was excreted via the kidney and urinary tract excretion and hepatobiliary excretion systems as excretion routes. Compared with [$^{18}$F]FMISO, compound 1 had low physiological accumulation in the liver as an excretion route, and it is therefore suggested that it can visualize a hypoxic lesion within a tumor in liver cancer. It was also found from the axial tomographic image (FIG. 11) that 60 minutes after administration there was tumor-specific accumulation separated from normal tissue such as muscle.

From the coronal tomographic images (FIG. 12), 60 minutes after administration intense accumulation of compound 2 and compound 3 was found in the bladder and accumulation thereof was found in the intestinal tract. Furthermore, it was confirmed that, as for compound 1, there was accumulation of compound 3 in the gallbladder. These results show that compound 2 was excreted mainly via the kidney and urinary tract system as an excretion route and compound 3 was excreted via the kidney and urinary tract system and the hepatobiliary system as for compound 1. Compared with [$^{18}$F]FMISO, compound 2 and compound 3 had low physiological accumulation in the liver as an excretion route, and it is therefore suggested that they can visualize a hypoxic lesion within a tumor in liver cancer. It was also confirmed from the axial tomographic image (FIG. 13) that 60 minutes after administration there was tumor-specific accumulation of compound 2 and compound 3 separated from normal tissue such as muscle.

Example 11

Measurement of SUV (Standardized Uptake Value) within Tumor and Calculation of Tumor/Normal Tissue Ratio (Method)

The maximum value for SUV within the tumor was measured using the axial tomographic images acquired in the Example 10. For all slice planes of an axial tomographic image where the tumor was visualized, a region of interest (hereinafter, called an ROI) was set for the entire tumor and measured. The axial tomographic image was formed from 61 slice planes, and the SUV that was the highest among the measured slice planes was defined as a maximum value for SUV 60 minutes after administration (SUV maximum value in tumor). On the other hand, the SUV of normal tissue was obtained using as a target site the lung and muscle tissue on the left body side, which was opposite to the side of the tumor-bearing model mouse where the tumor was implanted on the right body side, and an ROI was set for the entire left body side including the lung and muscle at 60 minutes after administration, and thereby the measurement was preformed. The average value for signal intensity within the ROI was determined, and the average value for values measured for the slice planes was defined as the average value for SUV in normal tissue. The tumor/normal tissue ratio was calculated using the following equation (1) and used as a subjective indicator with respect to contrast between the tumor and normal tissue.

$$\text{Tumor/normal tissue ratio} = \frac{\text{Maximum value of } SUV \text{ in tumor}}{\text{Average value of } SUV \text{ in normal tissue}} \quad (1)$$

(Results)

Table 2 shows the SUV maximum value and tumor/normal tissue ratio of compounds 1 to 3 and [$^{18}$F]FMISO. Compounds 1 to 3 all showed a higher tumor/normal tissue ratio than [$^{18}$F]FMISO at 60 minutes after administration. From these results, it is suggested that compound 1, compound 2, and compound 3 can give an image vizualizing a hypoxic region within a tumor with high contrast at an early time after administration.

TABLE 2

| Compound | SUV maximum value | Tumor/normal tissue ratio |
|---|---|---|
| [$^{18}$F]FMISO | 0.98 | 2.03 |
| Compound 1 | 0.58 | 2.34 |
| Compound 2 | 0.31 | 2.68 |
| Compound 3 | 0.53 | 2.40 |

Example 1

Confirmation of Localization of Accumulation within Tumor of Each of the Labeled Compounds In order to evaluate whether or not the compound related to the present invention could visualize a hypoxic region of a tumor, the following experiment was carried out using compounds 1 to 3 and [$^{18}$F]FMISO.

(Method)

Localization of accumulation of each of the labeled compounds within a tumor was confirmed by autoradiography. After PET imaging of a tumor-bearing model mouse prepared by the method of Example 11 was completed, it was sacrificed by blood-letting by cardiocentesis, immediately thereafter the tumor was sampled, and tissue sections (thickness: 10 μm) were prepared using a cryostat (model: CM3050, manufactured by Leica). For autoradiography measurement, while taking into consideration the short half-life of $^{18}$F, an unfixed fresh frozen section, which did not require much time for preparation of a tumor tissue section, was used. After exposing an imaging plate to this tumor tissue section for 8 to 10 hours, an image was captured using a bioimaging analyzer (model: BAS-2500, manufactured by FUJIFILM). The image thus captured was subjected to image analysis using image analysis software.

Separately, as a method for confirming a hypoxic region within a tumor, the same section after decay of radioactivity was subjected to immunohistochemical staining using pimonidazole that is a hypoxic marker, by the following procedure. After fixation and activation of the tumor tissue section, a rabbit polyclonal anti-pimonidazole antibody (obtained from: Hypoxyprobe, Inc., 1:200) as a primary antibody and a biotin-labeled anti-rabbit antiserum as a secondary antibody, which reacts with the primary antibody, were reacted with the tumor tissue section, and subsequently HRP (horseradish peroxidase) activity was detected by a color reaction with DAB (3,3'-diaminobenzidine) as a substrate using HRP-labeled streptavidin, which reacts with the secondary antibody, thus identifying a hypoxic region of the tumor tissue section. Furthermore, nuclear counterstaining, which stains the cell nucleus, employed Mayer's hematoxylin. One adjacent section from consecutive sliced sections was used as a negative control, the same experiment as above was carried out without reacting the primary antibody, and it was confirmed that no non-specific reaction between the tumor tissue section and any component other than the primary antibody was observed. An entire image of a sample image obtained by immunohistochemical staining was acquired using a microscope system (model: BZ-9000, manufactured by Keyence Corporation). The entire image thus acquired was subjected to image processing, and a pimonidazole-positive site showing a hypoxic region was extracted.
(Results)

Figure 14:
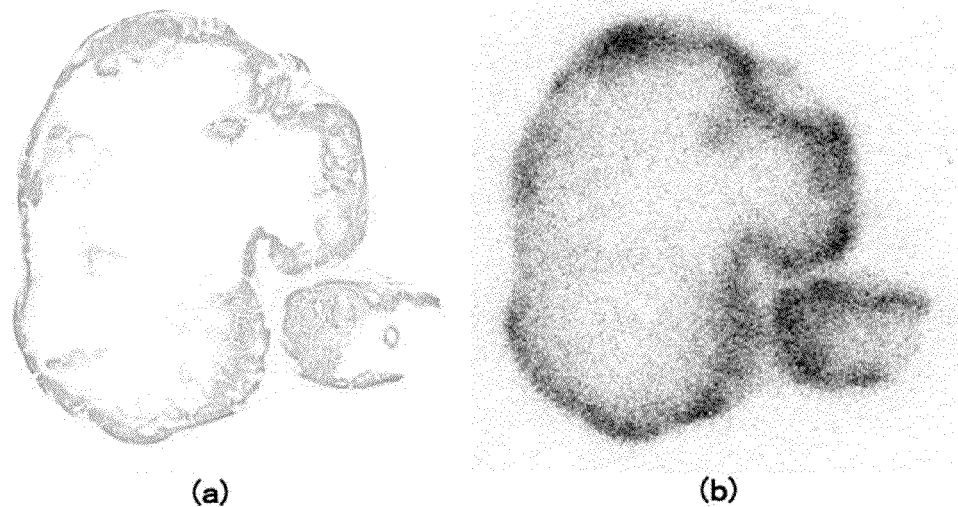
FIG. 14(a) is an immunohistochemical staining image.
FIG. 14(b) is autoradiography of accumulation of 1-(2,2-dihydroxymethyl-3-[$^{18}$F]fluoropropyl)-2-nitroimidazole in a tumor.
Figure 15:
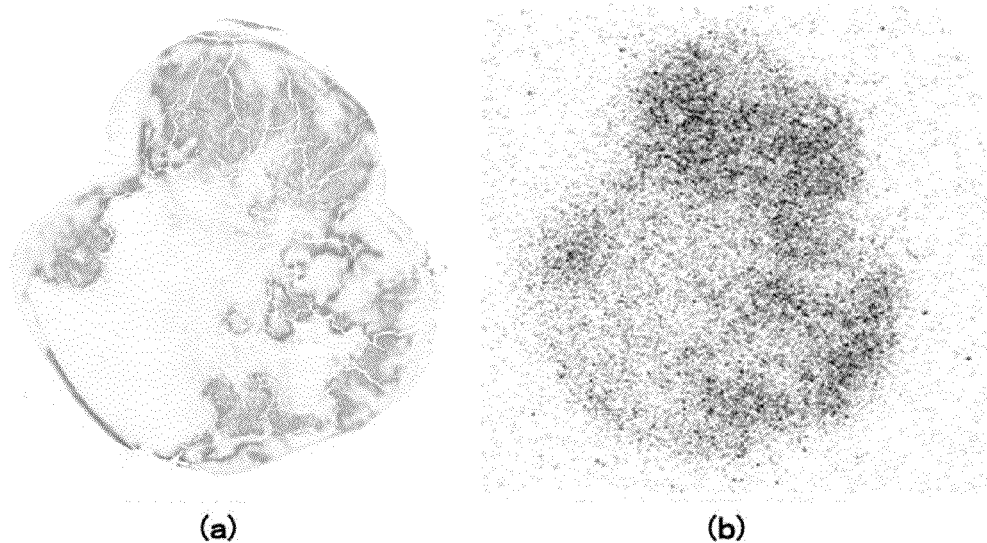
FIG. 15 (b) is autoradiography of accumulation of 1-(2,2-dihydroxymethyl-3-[$^{18}$F]fluoropropyl)-4-hydroxymethyl-2-nitroimidazole in a tumor.
Figure 16:
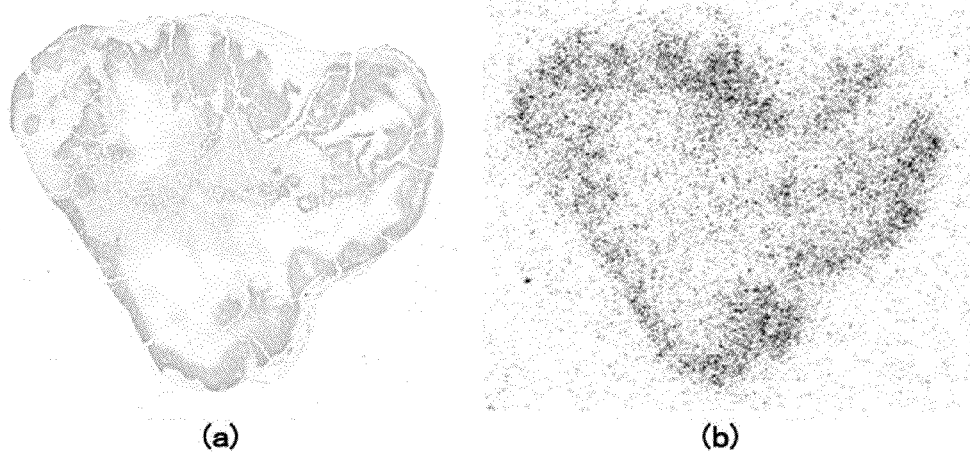
FIG. 16(a) is a diagram showing an immunohistochemical staining image.
FIG. 16(b) is autoradiography of accumulation of 1-(3,3-dihydroxymethyl-4-[$^{18}$F]fluorobutyl)-2-nitroimidazole in a tumor.
Figure 17:
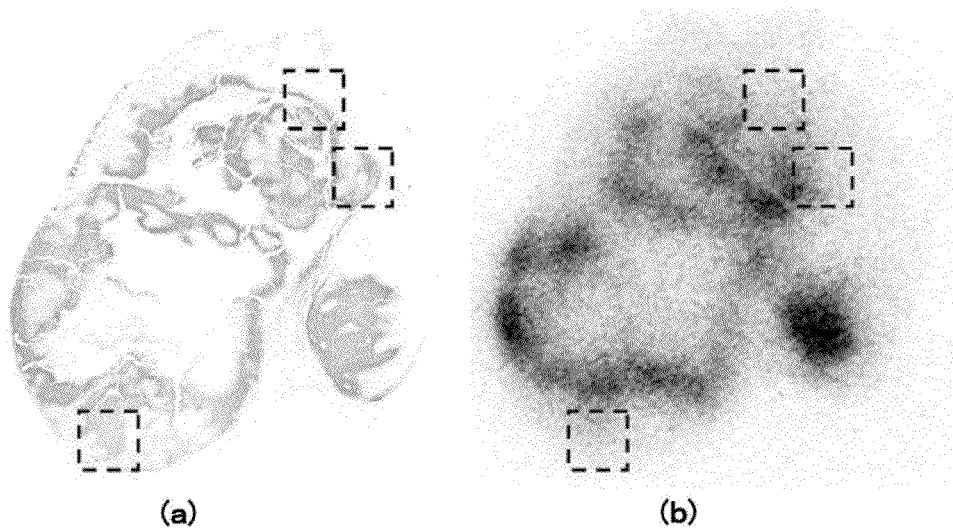
FIG. 17(a) is an immunohistochemical staining image.
FIG. 17(b) is autoradiography of accumulation of [$^{18}$F] FMISO in a tumor.

The results are shown in FIG. 14 to 17. FIG. 14(b) shows autoradiography of the accumulation of compound 1 within the tumor, and FIG. 14(a) shows an immunohistochemical staining image of the same section as for FIG. 14(b). FIG. 15(b) shows autoradiography of the accumulation of compound 2 within the tumor, and FIG. 15(a) shows an immunohistochemical staining image of the same section as for FIG. 15(b). FIG. 16 (b) shows autoradiography of the accumulation of compound 3 within the tumor, and FIG. 16(a) shows an immunohistochemical staining image of the same section as for FIG. 16(b). FIG. 17(b) shows autoradiography of the accumulation of [$^{18}$F]FMISO within the tumor, and FIG. 17 (a) shows an immunohistochemical staining image of the same section as for FIG. 17(b). As shown in FIGS. 14 to 16, the sites where compounds 1 to 3 accumulated coincided visually with localization of pimonidazole that is a hypoxic marker. On the other hand, as shown in FIG. 17, there were places (circled by broken lines in FIG. 17) where the site where [$^{18}$F]FMISO was accumulated did not visually coincide with localization of pimonidazole that is a hypoxic marker.

Example 13

Correlation Between Signal Intensity of Each of the Labeled Compounds in Autoradiographic Image and Localization of Hypoxic Environment In order to evaluate whether or not the compound related to the present invention can quantitatively visualize a hypoxic region of a tumor, the following experiment was carried out using compounds 1 to 3 and [$^{18}$F]FMISO.
(Method)

Using a microscope system (model: BZ-9000, Keyence Corporation) a high magnification image of a pimonidazole-positive site was acquired using the entire image of a pathology image obtained by immunohistochemical staining in the Example 12 and a 10× objective lens. The high magnification image was formed with respect to a randomly selected image region. At the same time the image acquisition site was recorded as a navigation image by use of the navigation function of the microscope system. The acquired high magnification image was subjected to image processing, and a pimonidazole-positive area present in the high magnification image was determined.

The autoradiographic image and the stained image of each labeled compound used were those acquired in the Example 12. The resolution of the navigation image was made to match the resolution of the autoradiographic image, and the geometrical positions of two images were aligned using image analysis software.

In the autoradiographic image, an ROI was set for the site that coincided with the high magnification image acquisition site, and the PSL value (Photo-Stimulated Luminescence value) of the ROI was determined. Furthermore, an ROI was set for a site of the same image that contained no sample, and the PSL value thereof was defined as the background. The PSL value of the background was subtracted from the PSL value of the high magnification image acquisition site to obtain the net PSL value. The hypoxic marker pimonidazole-positive area was plotted on the abscissa and the PSL value in the autoradiographic image on the ordinate, and the correlation factor was determined. This series of operations was carried out for each of the labeled compounds.
(Results)

Figure 18:
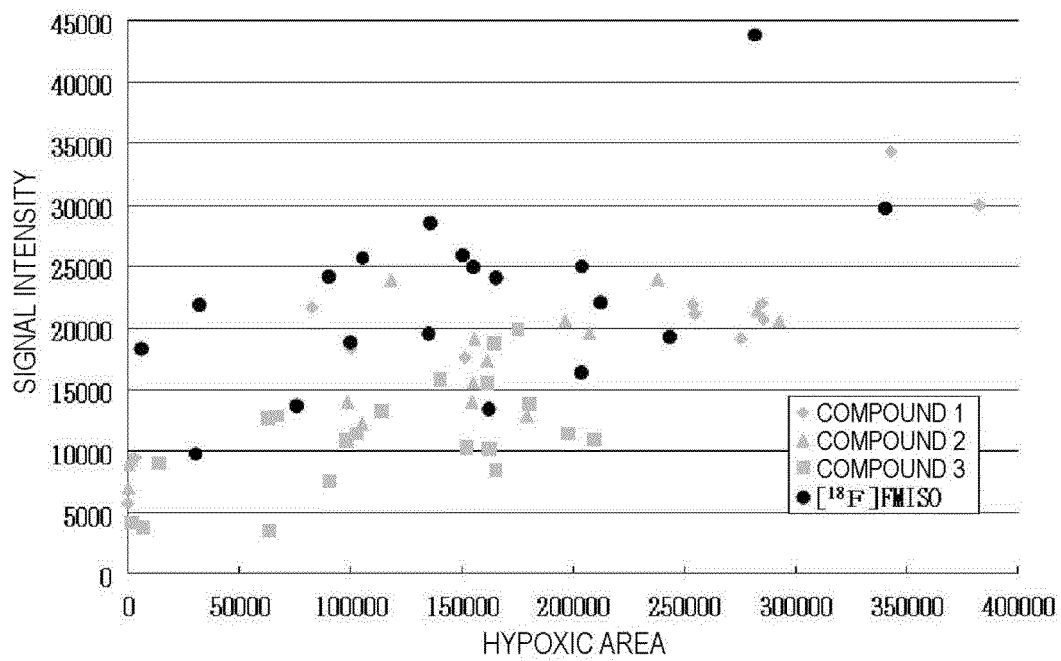
FIG. 18 is a chart showing the correlation between area of a hypoxic region and signal intensity in autoradiography of accumulation of 1-(2,2-dihydroxymethyl-3-[$^{18}$F]fluoropropyl)-2-nitroimidazole, 1-(2,2-dihydroxymethyl-3-[$^{18}$F]fluoropropyl)-4-hydroxymethyl-2-nitroimidazole, 1-(3,3-dihydroxymethyl-4-[$^{18}$F]fluorobutyl)-2-nitroimidazole, and [$^{18}$F]FMISO in a tumor.

The results are shown in FIG. 18 and Table 3. FIG. 18 is a chart showing the correlation between the signal intensity and the area of a hypoxic region in autoradiography for the accumulation of compounds 1 to 3 and [$^{18}$F]FMISO within the tumor. Table 3 shows the correlation factor between the immunohistological image and autoradiography. As is clear from FIG. 18, in the case of [$^{18}$F]FMISO, places where localization of pimonidazole that is a hypoxic marker, was observed sometimes showed a low PSL value, and there were some places where the PSL value and the hypoxic region (position of localization of pimonidazole) did not visually coincide with each other. As is also clear from FIG. 18 and Table 3, there were large variations in the plots of [$^{18}$F]FMISO in a scatter chart where the proportion occupied by the hypoxic environment and the intensity of accumulation corresponded. On the other hand, the accumulation of each of the labeled compounds showed a high PSL value in places where localization of the hypoxic marker was observed, thus exhibiting visual coincidence, which was similar to the results in Example 12. As is clear from FIG. 18, there was a correlation between the intensity of accumulation of each of the labeled compounds and the proportion occupied by the hypoxic environment at the same position. Furthermore, all of the labeled compounds related to the present invention exhibited a higher correlation factor than that of [$^{18}$F]FMISO. These results suggest that the intensity of accumulation of each of the labeled compounds in a tumor more quantitatively reflects the level of a hypoxic region within a tumor than does [$^{18}$F]FMISO.

TABLE 3

| Compound | Correlation coefficient |
|---|---|
| [$^{18}$F]FMISO | 0.55 |
| Compound 1 | 0.85 |
| Compound 2 | 0.80 |
| Compound 3 | 0.61 |

Example 14

Examination of Distribution of Each Labeled Compound within Body

The biodistribution of compounds 1 to 3 and [$^{18}$F]FMISO in a tumor and each of the organs of a tumor-bearing mouse was measured.
(Method)

Tumor-bearing model mice used in this experiment were the same as those prepared in Example 10, and 3 or 4 cases that had attained a tumor volume of 200 to 400 mm³ were selected from each group. The tumor-bearing model mouse was placed under isoflurane anesthesia, pimonidazole that is a hypoxic marker, was administered via a tail vein, and at 10 minutes thereafter, the respective labeled compound was administered. The tumor-bearing model mouse was sacrificed at 60 minutes and 120 minutes after administration. All of the tumor-bearing model mice were sacrificed by bloodletting from the abdominal aorta or by cardiocentesis, and dissection was carried out immediately thereafter. Other than the tumor, the blood, heart, lung, stomach, liver, gallbladder, kidney, small intestine and large intestine, muscle, and urine were sampled, and the other tissues were defined as the remaining whole body. After the weight of each tissue sampled was measured, the amount of radioactivity of the tissue was measured using a gamma counter, and the biodistribution of each of the labeled compounds was compared by converting it into % ID/g (% injection dose/g organ) of each tissue.

In order to examine a hypoxic state within the tumor, immunohistochemical staining of the sample tumor was carried out so as to ascertain whether or not the interior of the tumor was hypoxic. The sampled tumor was fixed using a 20% formalin buffer, and a paraffin block was prepared using an automatic paraffin-embedding apparatus (model: VIP-5-Jr-J0, Sakura Finetek). A slice (thickness: 3 μm) was prepared by means of a microtome (model: Tissue-Tek Feather Trustome, Sakura Finetek). Immunohistochemical staining was carried out by the same method as in Example 12.

(Results)

The results are shown in Table 4 and Table 5. Table 4 shows % ID/g for each tissue at 60 minutes after administration. Table 5 shows % ID/g for each tissue at 120 minutes after administration, but in Tables 4 and 5 urine is given as % ID. Furthermore, in Tables 4 and 5, T/B denotes tumor/blood ratio, and T/M denotes tumor/muscle ratio. The radioaccumulation of each of the labeled compounds in the tumor in the tumor-bearing model mouse was lower than that of [$^{18}$F]FMISO, but the distribution concentrations of compound 1 and compound 3 in the blood were 1.70% ID/g and 2.81% ID/g respectively at 60 minutes after administration of the respective labeled compounds, and decreased to 0.75% ID/g and 1.14% ID/g respectively at 120 minutes after administration of the respective labeled compounds. Furthermore, the distribution concentrations in the urine were 62.13% ID and 45.80% ID respectively at 60 minutes after administration of the respective labeled compounds, and increased to 77.76% ID and 68.78% ID respectively at 120 minutes after administration. From these results, it was confirmed that compounds 1 and compound 3 had rapid blood clearance and urinary excretion compared with [$^{18}$F]FMISO. Furthermore, compound 2 exhibited a distribution concentration of 0.60% ID/g for blood and 80.42% ID for urine at 60 minutes after administration of the labeled compound. Thus, it was confirmed that the blood clearance and urinary excretion thereof were even more rapid. Moreover, the tumor blood ratio between 60 minutes after administration and 120 minutes after administration of each of the labeled compounds was higher than for [$^{18}$F]FMISO. From the result of immunohistochemical staining, it was confirmed that the interior of the tumor was hypoxic.

TABLE 4

| | | Blood | Heart | Lung | Liver | Stomach | Small intestine | Large intestine | Gall bladder | Kidney | Muscle | Urine | Tumor | T/B | T/M |
|---|---|---|---|---|---|---|---|---|---|---|---|---|---|---|---|
| Compound 1 | Mean | 1.70 | 2.35 | 1.96 | 3.34 | 1.53 | 3.72 | 3.71 | 26.34 | 4.23 | 1.71 | 62.13 | 2.38 | 1.42 | 1.39 |
| | Standard error | 0.14 | 0.25 | 0.12 | 0.18 | 0.15 | 0.29 | 0.18 | 12.62 | 0.90 | 0.06 | 1.74 | 0.07 | 0.08 | 0.05 |
| Compound 2 | Mean | 0.60 | 1.32 | 0.89 | 1.14 | 0.48 | 2.35 | 0.96 | 7.54 | 1.86 | 1.25 | 80.42 | 1.13 | 2.11 | 0.91 |
| | Standard error | 0.09 | 0.12 | 0.04 | 0.03 | 0.03 | 0.07 | 0.05 | 1.54 | 0.05 | 0.08 | 0.88 | 0.02 | 0.47 | 0.07 |
| Compound 3 | Mean | 2.81 | 3.46 | 2.92 | 4.46 | 1.99 | 4.68 | 5.40 | 16.71 | 9.95 | 2.66 | 45.80 | 2.05 | 0.86 | 0.87 |
| | Standard error | 0.93 | 1.09 | 0.83 | 1.90 | 0.82 | 1.15 | 0.71 | 9.17 | 3.35 | 0.79 | 12.76 | 0.31 | 0.20 | 0.18 |
| [$^{18}$F] FMISO | Mean | 4.45 | 5.12 | 4.41 | 5.84 | 4.17 | 5.76 | 13.76 | 12.92 | 8.52 | 3.80 | 34.98 | 4.71 | 1.06 | 1.24 |
| | Standard error | 0.14 | 0.05 | 0.05 | 0.15 | 0.34 | 0.06 | 1.51 | 1.25 | 1.79 | 0.08 | 5.09 | 0.09 | 0.02 | 0.01 |

TABLE 5

| | | Blood | Heart | Lung | Liver | Stomach | Small intestine | Large intestine | Gall bladder | Kidney | Muscle | Urine | Tumor | T/B | T/M |
|---|---|---|---|---|---|---|---|---|---|---|---|---|---|---|---|
| Compound 1 | Mean | 0.75 | 1.90 | 0.89 | 4.31 | 0.88 | 2.78 | 2.37 | 8.21 | 2.91 | 0.84 | 77.76 | 1.65 | 2.47 | 2.03 |
| | Standard error | 0.14 | 0.21 | 0.14 | 2.79 | 0.03 | 0.24 | 0.65 | 0.78 | 0.86 | 0.09 | 3.85 | 0.06 | 0.45 | 0.18 |
| Compound 2 | Mean | 0.25 | 0.74 | 0.34 | 0.54 | 0.25 | 1.63 | 0.88 | 7.33 | 0.82 | 0.47 | 90.92 | 0.78 | 3.18 | 1.68 |
| | Standard error | 0.01 | 0.12 | 0.02 | 0.04 | 0.03 | 0.12 | 0.12 | 2.28 | 0.05 | 0.05 | 0.24 | 0.02 | 0.06 | 0.10 |
| Compound 3 | Mean | 1.14 | 1.82 | 1.38 | 2.13 | 1.26 | 3.66 | 6.89 | 15.45 | 9.20 | 1.44 | 68.78 | 1.93 | 2.11 | 1.62 |
| | Standard error | 0.55 | 0.97 | 0.73 | 1.17 | 0.68 | 1.16 | 1.58 | 3.95 | 7.68 | 0.66 | 14.09 | 0.49 | 0.43 | 0.31 |
| [$^{18}$F] FMISO | Mean | 2.26 | 3.33 | 2.69 | 3.85 | 1.85 | 4.63 | 21.16 | 43.43 | 3.89 | 2.29 | 41.45 | 4.28 | 1.91 | 1.88 |
| | Standard error | 0.16 | 0.38 | 0.27 | 0.34 | 0.38 | 0.36 | 1.79 | 29.12 | 0.57 | 0.18 | 2.15 | 0.19 | 0.07 | 0.07 |

The above results suggest that the radioactive fluorine-labeled compound related to the present invention can give an image that reflects a hypoxic state within a tumor with high contrast at a comparatively early time after administration.

Embodiments and Examples of the present invention are described above, but they are only illustrations of the present invention, and various constitutions other than the above may be employed.

INDUSTRIAL APPLICABILITY

The radioactive fluorine-labeled compound related to the present invention may be applied in the field of imaging diagnostic agents in nuclear medicine.

The invention claimed is:

1. A compound represented by the following formula (1) or a salt thereof,

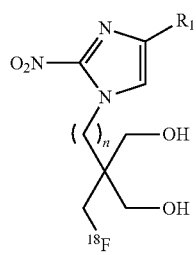

(1)

wherein in the formula (1), $R_1$ denotes a hydrogen atom, a methyl group, or a hydroxymethyl group, and n is an integer of 1 or 2.

2. A compound represented by the following formula (2) or a salt thereof,

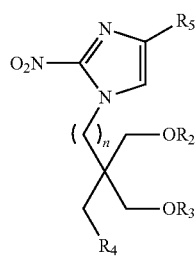

(2)

wherein in the formula (2), $R_2$ and $R_3$ denote the same or mutually different hydroxy protecting groups, or $R_2$ and $R_3$ together denote a diol protecting group, $R_4$ denotes a non-radioactive halogen, a trialkylammonium having 3 to 12 carbon atoms, a straight-chain or branched alkylsulfonyloxy group having 1 to 10 carbon atoms, a straight-chain or branched haloalkylsulfonyloxy group having 1 to 10 carbon atoms, a substituted or unsubstituted arylsulfonyloxy group, or a dialkylsulfonium group having 2 to 8 carbon atoms, $R_5$ denotes a hydrogen atom, a methyl group, or —$CH_2OR_6$, $R_6$ denotes a hydroxy protecting group, and n is an integer of 1 or 2.

3. The compound according to claim 2, wherein $R_2$ and $R_3$ together denote a methylene group, a 1-methylethan-1,1-diyl group, an ethan-1,1-diyl group, or a 1-phenylmethan-1,1-diyl group, resulting in formation of a 1,3-dioxane ring.

4. The compound according to claim 2, wherein $R_4$ is a non-radioactive bromine atom or iodine atom, or a p-toluenesulfonyloxy group.

5. A radioactive pharmaceutical composition comprising the compound or a salt thereof according to claim 1.

6. The radioactive pharmaceutical composition according to claim 5, wherein it is used for imaging a hypoxic region.

7. The radioactive pharmaceutical composition according to claim 5, wherein it is used for imaging a tumor.

8. A method for producing a compound represented by the formula (1) or a salt,

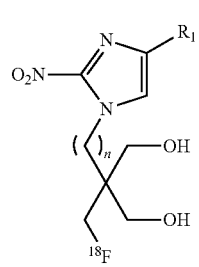

(1)

wherein in the formula (1), $R_1$ denotes a hydrogen atom, a methyl group, or a hydroxymethyl group, and n is an integer of 1 or 2, which comprises:
a step of producing a compound represented by the following formula (3) or a salt thereof from the compound represented by the formula (2) or a salt thereof,

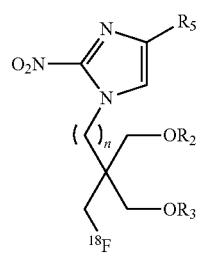

(3)

wherein in the formula (3), $R_2$ and $R_3$ denote the same or mutually different hydroxy protecting groups, or $R_2$ and $R_3$ together denote a diol protecting group, $R_5$ denotes a hydrogen atom, a methyl group, or —$CH_2OR_6$, $R_6$ denotes a hydroxy protecting group, and n is an integer of 1 or 2, and

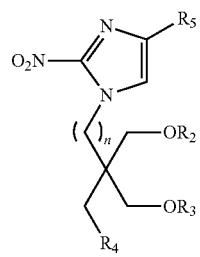

(2)

wherein in the formula (2), $R_2$ and $R_3$ denote the same or mutually different hydroxy protecting groups, or $R_2$ and $R_3$ together denote a diol protecting group, $R_4$ denotes a non-radioactive halogen, a trialkylammonium having 3 to 12 carbon atoms, a straight-chain or branched alkylsulfonyloxy group having 1 to 10 carbon atoms, a straight-chain or branched haloalkylsulfonyloxy group having 1 to 10 carbon atoms, a substituted or unsubstituted arylsulfonyloxy group, or a dialkylsulfonium group having 2 to 8 carbon atoms, $R_5$ denotes a hydrogen atom, a methyl group, or —$CH_2OR_6$, $R_6$ denotes a hydroxy protecting group, and n is an integer of 1 or 2, and a step of deprotecting the mutually independent hydroxy protecting groups or diol protecting group of $R_2$ and $R_3$ in the formula (3).

9. The compound according to claim 3, wherein $R_4$ is a non-radioactive bromine atom or iodine atom, or a p-toluenesulfonyloxy group.

* * * * *